US010137167B2

(12) United States Patent
Klein et al.

(10) Patent No.: US 10,137,167 B2
(45) Date of Patent: *Nov. 27, 2018

(54) METHODS COMPRISING DESMOPRESSIN

(71) Applicant: Ferring B.V., Hoofddorp (NL)

(72) Inventors: Bjarke Mirner Klein, Frederiksberg (DK); Jens Peter Norgaard, Frederiksberg (DK)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/143,866

(22) Filed: Dec. 30, 2013

(65) Prior Publication Data

US 2014/0113863 A1    Apr. 24, 2014

Related U.S. Application Data

(63) Continuation of application No. 12/732,161, filed on Mar. 25, 2010, which is a continuation-in-part of application No. 12/469,801, filed on May 21, 2009.

(60) Provisional application No. 61/055,120, filed on May 21, 2008.

(51) Int. Cl.
*A61K 38/11* (2006.01)
*A61K 9/00* (2006.01)
*A61K 38/08* (2006.01)
*A61P 13/10* (2006.01)

(52) U.S. Cl.
CPC ............ *A61K 38/11* (2013.01); *A61K 9/0056* (2013.01); *A61K 38/08* (2013.01); *A61P 13/10* (2018.01)

(58) Field of Classification Search
None
See application file for complete search history.

(56) References Cited

U.S. PATENT DOCUMENTS

| | | |
|---|---|---|
| 3,989,816 A | 11/1976 | Rajadhyaksha |
| 4,263,283 A | 4/1981 | Cort |
| 4,285,858 A | 8/1981 | Cort et al. |
| 4,316,893 A | 2/1982 | Rajadhyaksha |
| 4,405,616 A | 9/1983 | Rajadhyaksha |
| 4,557,934 A | 12/1985 | Cooper |
| 4,588,580 A | 5/1986 | Gale et al. |
| 4,783,450 A | 11/1988 | Fawzi et al. |
| 4,863,737 A | 9/1989 | Stanley et al. |
| 4,878,892 A | 11/1989 | Sibalis et al. |
| 5,047,398 A | 9/1991 | Hagstam et al. |
| 5,091,186 A | 2/1992 | Miranda et al. |
| 5,135,480 A | 8/1992 | Bannon et al. |
| 5,298,256 A | 3/1994 | Flockhart et al. |
| 5,441,490 A | 8/1995 | Svedman |
| 5,466,464 A | 11/1995 | Masaki et al. |
| 5,482,931 A | 1/1996 | Harris et al. |
| 5,498,598 A | 3/1996 | Harris |
| 5,500,413 A | 3/1996 | Larsson et al. |
| 5,527,288 A | 6/1996 | Gross et al. |
| 5,534,496 A | 7/1996 | Lee et al. |
| 5,596,078 A | 1/1997 | Andersson et al. |
| 5,611,806 A | 3/1997 | Jang |
| 5,631,246 A | 5/1997 | Hashemi et al. |
| 5,674,850 A | 10/1997 | Larsson et al. |
| 5,698,516 A | 12/1997 | Nilsson et al. |
| 5,707,648 A | 1/1998 | Yiv |
| 5,726,287 A | 3/1998 | Andersson et al. |
| 5,763,398 A | 6/1998 | Bengtsson |
| 5,763,405 A | 6/1998 | Fjellestad-Paulsen et al. |
| 5,763,407 A | 6/1998 | Larsson et al. |
| 5,780,434 A | 7/1998 | Fjellestad-Paulsen et al. |
| 5,821,230 A | 10/1998 | Jiang et al. |
| 5,843,016 A | 12/1998 | Lugnami et al. |
| 5,848,991 A | 12/1998 | Gross et al. |
| 5,906,831 A | 5/1999 | Larsson et al. |
| 5,922,680 A | 7/1999 | Fjellestad-Paulsen et al. |
| 5,932,745 A | 8/1999 | Dushin et al. |
| 5,948,433 A | 9/1999 | Burton et al. |
| 5,985,835 A | 11/1999 | Larsson et al. |
| 5,990,273 A | 11/1999 | Andersson et al. |
| 6,010,478 A | 1/2000 | Bellhouse et al. |
| 6,090,803 A | 7/2000 | Failli et al. |
| 6,139,866 A | 10/2000 | Chono et al. |
| 6,143,722 A | 11/2000 | Melin et al. |
| 6,148,232 A | 11/2000 | Avrahami |
| 6,194,407 B1 | 2/2001 | Failli et al. |
| 6,235,900 B1 | 5/2001 | Failli et al. |
| 6,248,363 B1 | 6/2001 | Patel et al. |
| 6,268,360 B1 | 7/2001 | Failli et al. |
| 6,297,234 B1 | 10/2001 | Failli et al. |
| 6,314,317 B1 | 11/2001 | Willis |
| 6,322,532 B1 | 11/2001 | D'Sa et al. |
| 6,344,451 B1 | 2/2002 | Steffan et al. |
| 6,348,486 B1 | 2/2002 | Argentieri et al. |
| 6,406,455 B1 | 6/2002 | Willis et al. |
| 6,490,483 B2 | 12/2002 | Willis |
| 6,511,974 B1 | 1/2003 | Dusza et al. |
| 6,558,695 B2 | 5/2003 | Luo et al. |
| 6,564,093 B1 | 5/2003 | Ostrow et al. |
| 6,616,627 B2 | 9/2003 | Willis et al. |
| 6,620,807 B1 | 9/2003 | Steffan et al. |
| 6,664,249 B1 | 12/2003 | Ashworth et al. |

(Continued)

FOREIGN PATENT DOCUMENTS

| | | |
|---|---|---|
| CN | 1739513 A | 5/2006 |
| EP | 0 278 474 A1 | 8/1988 |

(Continued)

OTHER PUBLICATIONS

"Minirin Nasal Spray". Ferring Pharmaceuticals. Internet document <<http://www.medsafe.gov.nz/Consumers/CMI/m/MinirinNSpray.htm>&g- t; May 3, 2001; accessed Sep. 15, 2008; 4 pages.

(Continued)

*Primary Examiner* — Olga N Chernyshev
(74) *Attorney, Agent, or Firm* — Finnegan, Henderson, Farabow, Garrett & Dunner, LLP

(57) ABSTRACT

The present disclosure is directed to reducing nocturnal voids by administering a dose of desmopressin over a minimum treatment period compared to before administration, and maintaining or improving the reduction of nocturnal voids over the minimum treatment period.

13 Claims, 4 Drawing Sheets

(56) References Cited

U.S. PATENT DOCUMENTS

| | | |
|---|---|---|
| 6,693,082 B2 | 2/2004 | Alonso et al. |
| 6,720,001 B2 | 4/2004 | Chen et al. |
| 6,723,077 B2 | 4/2004 | Pickup et al. |
| 6,746,678 B1 | 6/2004 | Shapiro |
| 6,893,655 B2 | 5/2005 | Flanigan et al. |
| 6,903,091 B2 | 6/2005 | Falli et al. |
| 6,930,932 B2 | 8/2005 | Rentschler |
| 6,939,324 B2 | 9/2005 | Gonnelli et al. |
| 6,945,952 B2 | 9/2005 | Kwon |
| 6,960,184 B2 | 11/2005 | Willis et al. |
| 7,018,653 B2 | 3/2006 | Wannerberger et al. |
| 7,022,340 B2 | 4/2006 | Lomryd et al. |
| 7,022,699 B2 | 4/2006 | Failli et al. |
| 7,027,478 B2 | 4/2006 | Ackley |
| 7,053,083 B2 | 5/2006 | Failli et al. |
| 7,060,708 B2 | 6/2006 | Piccariello et al. |
| 7,074,781 B2 | 7/2006 | Ashworth et al. |
| 7,090,763 B2 | 8/2006 | Gottschling et al. |
| 7,094,545 B2 | 8/2006 | Lomryd et al. |
| 7,097,631 B2 | 8/2006 | Trautman et al. |
| 7,097,776 B2 | 8/2006 | Govinda Raju |
| 7,138,393 B2 | 11/2006 | Molinari et al. |
| 7,150,409 B2 | 12/2006 | Gonnelli et al. |
| 7,153,845 B2 | 12/2006 | Levine et al. |
| 7,180,274 B2 | 2/2007 | Chen et al. |
| 7,182,747 B2 | 2/2007 | Kwon |
| 7,187,969 B2 | 3/2007 | Willis |
| 7,383,084 B2 | 6/2008 | Stern et al. |
| 7,405,203 B2 | 7/2008 | Fein |
| 7,560,429 B2 | 7/2009 | Nilsson et al. |
| 7,579,321 B2 | 8/2009 | Fein |
| 8,007,830 B2 | 8/2011 | Down |
| 2002/0013262 A1 | 1/2002 | Alonso et al. |
| 2002/0016562 A1 | 2/2002 | Cormier et al. |
| 2002/0082543 A1 | 6/2002 | Park et al. |
| 2002/0107265 A1 | 8/2002 | Chen et al. |
| 2002/0128599 A1 | 9/2002 | Cormier et al. |
| 2002/0178196 A1 | 11/2002 | Monier |
| 2002/0198191 A1 | 12/2002 | Failli et al. |
| 2003/0018024 A1 | 1/2003 | Failli et al. |
| 2003/0054044 A1 | 3/2003 | Potter et al. |
| 2003/0087892 A1 | 5/2003 | Ashworth et al. |
| 2003/0119728 A1 | 6/2003 | Scheidl et al. |
| 2003/0134845 A1 | 7/2003 | Molinari et al. |
| 2004/0018241 A1 | 1/2004 | Houze et al. |
| 2004/0038962 A1 | 2/2004 | Ashworth et al. |
| 2004/0063628 A1 | 4/2004 | Piccariello et al. |
| 2004/0115167 A1 | 6/2004 | Cormier et al. |
| 2004/0138098 A1 | 7/2004 | Fein |
| 2004/0138610 A1 | 7/2004 | Cormier et al. |
| 2004/0220080 A1 | 11/2004 | Lomryd et al. |
| 2004/0242686 A1 | 12/2004 | Isawa et al. |
| 2004/0249339 A1 | 12/2004 | Willis et al. |
| 2004/0265365 A1 | 12/2004 | Daddona et al. |
| 2005/0004103 A1 | 1/2005 | Koshio et al. |
| 2005/0019392 A1 | 1/2005 | Lomryd et al. |
| 2005/0075328 A1 | 4/2005 | Failli et al. |
| 2005/0089554 A1 | 4/2005 | Cormier et al. |
| 2005/0096586 A1 | 5/2005 | Trautman et al. |
| 2005/0106226 A1 | 5/2005 | Cormier et al. |
| 2005/0153873 A1 | 7/2005 | Chan et al. |
| 2005/0154350 A1 | 7/2005 | Willis et al. |
| 2005/0158378 A1 | 7/2005 | Wannerberger et al. |
| 2005/0232997 A1 | 10/2005 | Nilsson et al. |
| 2006/0025387 A1 | 2/2006 | Hochman |
| 2006/0040970 A1 | 2/2006 | Izumimoto et al. |
| 2006/0093658 A1 | 5/2006 | Sathyan et al. |
| 2006/0122113 A1 | 6/2006 | Pinchasi et al. |
| 2006/0122170 A1 | 6/2006 | Koshio et al. |
| 2006/0154916 A1 | 7/2006 | Ashworth et al. |
| 2006/0161111 A1 | 7/2006 | Potter et al. |
| 2006/0183734 A1 | 8/2006 | Failli et al. |
| 2006/0189939 A1 | 8/2006 | Gonnelli et al. |
| 2006/0193825 A1 | 8/2006 | Musso et al. |
| 2006/0200069 A1 | 9/2006 | Cormier et al. |
| 2006/0233871 A1 | 10/2006 | Stern et al. |
| 2006/0240068 A1 | 10/2006 | Lomryd et al. |
| 2006/0241172 A1 | 10/2006 | Zhou et al. |
| 2006/0241176 A1 | 10/2006 | Stack et al. |
| 2006/0247276 A1 | 11/2006 | Gross et al. |
| 2006/0252696 A1 | 11/2006 | Lomryd et al. |
| 2006/0253061 A1 | 11/2006 | Anderson et al. |
| 2006/0258712 A1 | 11/2006 | Jacobson |
| 2006/0258714 A1 | 11/2006 | Heffernan et al. |
| 2006/0258739 A1 | 11/2006 | Ai et al. |
| 2007/0027427 A1 | 2/2007 | Trautman et al. |
| 2007/0032410 A1 | 2/2007 | Quay et al. |
| 2007/0117759 A1 | 5/2007 | Wannerberger et al. |
| 2007/0265207 A1 | 11/2007 | Fein |
| 2008/0274951 A1 | 11/2008 | Fein |
| 2009/0042970 A1 | 2/2009 | Herschkowitz et al. |

FOREIGN PATENT DOCUMENTS

| | | |
|---|---|---|
| EP | 0 517 211 A1 | 12/1992 |
| EP | 1 153 616 A1 | 11/2001 |
| EP | 1 428 526 A1 | 6/2004 |
| EP | 1 550 439 B1 | 3/2006 |
| EP | 1 530 987 B1 | 5/2006 |
| EP | 1 501 534 B1 | 7/2006 |
| GB | 1 548 022 | 7/1979 |
| GB | 2 111 423 A | 7/1983 |
| GB | 2 114 440 A | 8/1983 |
| WO | WO 1985/02119 A1 | 5/1985 |
| WO | WO 1991/01132 A1 | 2/1991 |
| WO | WO 1993/03751 A1 | 3/1993 |
| WO | WO 1994/12142 A1 | 6/1994 |
| WO | WO 1995/01185 A1 | 1/1995 |
| WO | WO 1997/48485 A1 | 12/1997 |
| WO | WO 2000/36353 A1 | 6/2000 |
| WO | WO 2000/44351 A1 | 8/2000 |
| WO | WO 2000/59423 A1 | 10/2000 |
| WO | WO 2000/61117 A1 | 10/2000 |
| WO | WO 2001/22319 A1 | 3/2001 |
| WO | WO 2001/60394 A1 | 8/2001 |
| WO | WO 2002/064193 A2 | 8/2002 |
| WO | WO 2002/074286 A1 | 9/2002 |
| WO | WO 2003/094885 A1 | 11/2003 |
| WO | WO 2003/094886 A2 | 11/2003 |
| WO | WO 2004/041153 A2 | 5/2004 |
| WO | WO 2005/041871 A2 | 5/2005 |
| WO | WO 2005/046646 A2 | 5/2005 |
| WO | WO 2005/046707 A1 | 5/2005 |
| WO | WO 2006/060106 A1 | 6/2006 |
| WO | WO 2006/138719 A2 | 12/2006 |
| WO | WO 2007/002523 A2 | 1/2007 |
| WO | WO 2007/083323 A2 | 7/2007 |
| WO | WO 2007/098945 A2 | 9/2007 |
| WO | WO 2007/127976 A2 | 11/2007 |
| WO | WO 2009/021007 A1 | 2/2009 |
| WO | WO 2009/143356 A1 | 11/2009 |

OTHER PUBLICATIONS

Agerso et al., "Pharmacokinetics and Renal Excretion of Desmopressin after Intravenous Administration to Healthy Subjects and Renally Impaired Patients," Br. J. Clin Pharmacol., 58(4):352-358 (2004).

Akerstedt et al., "A Prospective Study of Fatal Occupational Accidents—Relationship to Sleeping Difficulties and Occupational Factors," J Sleep Res, 11:69-71 (2002).

Anderson, "Gender Differences in Pharmacological Response," International Review of Neurobiology, 83:1-10 (2008).

Anderson, "Sex and Racial Differences in Pharmacological Response: Where is the Evidence? Pharmacogetics, Pharmacokinetics, and Pharmacodynamics," Journal of Women's Health, 14(1):19-31 (2005).

Asplund et al., "Desmospressin in Elderly Subjects with Increased Nocturnal Diuresis," Scand. J. Urol. Nephrol, 27:77-82 (1993).

Asplund et al., "Diurnal Variation in the Levels of Antidiuretic Hormone in the Elderly"; Journal of Internal Medicine; 229:131-134 (1991).

Asplund et al., "Nocturnal Micturition, Sleep and Well-being in Women Ages 40-64 Years," Maturitas, 24:73-81 (1996).

(56) References Cited

OTHER PUBLICATIONS

Asplund et al., "Oral Desmopressin for Nocturnal Polyuria in Elderly Subjects: A Double-blind, Placebo-controlled Randomized Exploratory Study," BJU International, 83:591-595 (1999).

Asplund, "Nocturia in Relation to Sleep, Health, and Medical Treatment in the Elderly," BJU International, 96(Suppl. 1):15-21 (2005).

Bae et al., "The Effects of Long-Term Administration of Oral Desmopressin on the Baseline Secretion of Antidiuretic Hormone and Serum Sodium Concentration for the Treatment of Nocturia: A Circadian Study," The Journal of Urology, 178:200-203 (Jul. 2007).

Baker et al., "Fall Injuries in the Elderly," Clin Geriatr Med, 1(Chapter 55):501-512 (1985).

Baylis et al., "Osmoregulation of Vasopressin Secretion and Thirst in Health and Disease," Clinical Endocrinology, 29:549-576 (1988).

Beck et al., "Chapter 55: Aging Changes in Renal Function", Hazzard WR et al., Editors; Principles of Geriatric Medicine and Gerontology, McGraw-Hill Book Co., pp. 555-564 (1990).

Blanker et al., "Normal Voiding Patterns and Determinants of Increased Diurnal and Nocturnal VoidingFrequency in Elderly Men," J Urol, 164:1201-1205 (2000).

Bodo et al., "Circadian Antidiuretic Hormone Variation in Elderly Men Complaining of Persistent Nocturia After Urinary Flow Obstruction Removal," Scandinavian J. Urol. Nephrol, 32:320-24 (1998).

Bogaert et al., "A Pharmacodynamic Study in Children with Primary Nocturnal Enuresis Using a New 'Melt' Orodispersible Formulation of Desmopressin," Neurology and Urodynamics, 24(5-6):578-579 (Jan. 1, 2005).

Bosch et al., "The Prevalence and Causes of Nocturia," The Journal of Urology, 184:440-446 (Aug. 2010).

Britton et al., "Prevalence of Urinary Symptoms in Men Over Age 60," Br. J. Urol, 66:175-176 (1990).

Brosen, "Gender Differences in Pharmacology," Science and Practice, 2408-2411.

Callreus et al., "Hyponatremia Idelderly Patients Treated with Desmopressin for Nocturia: a Review of a Case Series," Eur. J. Clin Pharmacol, 61:281-284 (2005).

Carrel et al., "X-Inactivation Profile Reveals Extensive Variability in X-linked Gene Expression in Females," Nature, 434:400-404 (2005).

Chute et al., "The Prevalence of Prostatism: A Population-based Survey of Urinary Symptoms," J. Urol, 150:85-89 (1993).

Claybaugh et al., "Effects of time of Day, Gender, and Menstrual Cycle Phase on the Human Response to a Water Load," Am. J. Physiol Regul Integr. Comp. Physiol., 279:R966-R973 (2000).

Copending U.S. Appl. No. 10/513,437, Advisory Action dated Aug. 7, 2008.

Copending U.S. Appl. No. 10/513,437, Final Office Action dated Nov. 15, 2007.

Copending U.S. Appl. No. 10/513,437, Notice of Allowability (Supplemental) dated Apr. 24, 2009.

Copending U.S. Appl. No. 10/513,437, Notice of Allowance dated Feb. 4, 2009.

Copending U.S. Appl. No. 10/513,487; Non-Final Office Action dated Mar. 27, 2007.

Copending U.S. Appl. No. 10/519,715, Office Action dated May 7, 2009.

Copending U.S. Appl. No. 10/519,715, Office Action dated Sep. 3, 2008.

Coyne et al., "The Prevalence of Nocturia and its Effect on Health-related Quality of Llife and Sleep in a Community Sample in the USA," BJU Int, 92:948-954 (2003).

Curran, "Silodosin Treatment of the Signs and Symptoms of Benign Prostatic Hyperplasia," Drugs, 71(7):897-907 (2011).

Cvetkovic et al., Desmopressin in Adults with Nocturia, Drugs, 66(1):99-107 (2005).

Diokno et al., "Prevalence of Urinary Incontinence and Other Urological Symptoms in the Noninstitutionalized Elderly," J Urol,136:1022-1025 (1986).

Dixon et al., "The Effect of DDAVP on Intravenous Urography", British Journal of Radiology, 54:484-487 (1981).

Fjellestad-Paulsen et al., "Comparison of Intranasal and Oral Desmopressin for Nocturnal Enuresis," Archives of Disease in Childhood, 62:674-677 (1987).

Fjellestad-Paulsen, A.M. Doctoral Dissertation entitled "Absorption and Metabolism of Neurophypophyseal Hormones, with special reference to Desmopressin (dDAVP), in Human Tissue and after Various Routes of Administration"; May 25, 1996.

Fultz et al., "Epidemiology of Urinary Symptoms in the Geriatric Population," Urol Clin North Am, 23:1-10 (1996).

George et al., "Diurnal Variation of Plasma Vasopressin in Man," J. Clin. Endocrin. Metab., 41:332-338 (1975).

Graugaard-Jensen et al., "Nocturia and Circadian Blood Pressure Profile in Healthy Elderly Male Volunteers," J. Urol., 176:1034-1039 (2006).

Graugaard-Jensen et al., "The Influence of Oral Contraceptives on Diurnal Urine Regulation," Int. Urogynecol J. 21(Suppl 1):S311-S313 (Aug. 23-27, 2010).

Grossman et al., "Two New Nodes of Desmopressin (DDAVP) Administration," British Medical Journal, p. 1215 (May 17, 1980).

Guchtenaere et al., "Oral Lyophylizate Formulation of Desmopressin: Superior Pharmacodynamics Compared to Tablet Due to Low Food Interaction," The Journal of Urology, 185:2308-2313 (Jun. 2011).

Guide National De Prescription Des Medicaments, "Quelques regles de prescription chez le sujet age," 1997, Editions Du Vidal, Paris, pp. 1047-1048.

Guide National De Presecription Des Medicaments,"Quelques Régles De Prescription Chez Le Sujet Âgé," 1997, Editions Du Vidal, Paris, p. 1046-1048.

Hakkinen, J. et al; "Incidence of nocturia in 50 to 80-year-old Finnish Men"; J Urol; 2006; vol. 176; pp. 2541-2545.

Hancock et al., "Race, Sex, and the Regulation of Urine Osmolatity: Observations Made During Water Deprivation," Am. J. Physiol. Regul. Integr. Comp. Physiol., 299:R977-R980 (2010).

Harris, "Clinical Experience with Desmopresson: Efficacy and safety in central diabetes insipidous and other conditions"; J. Pediatrics; 1989; vol. 114; No. 4; Part 2; pp. 711-718.

Hetta et al., "Mood Alterations and Sleep," Ann. Clin. Res., 17:252-256 (1985).

Hvistendahl et al., "Gender Differences in Nighttime Plasma Arginine Vasporessin and Delayed Compensatory Urine Output in the Elderly Population After Desmopressin," The Journal of Urology, 178:2671-2676 (2007).

Hvistendahl et al., "The Pharmacokinetics of 400 μg of Oral Desmopressin in Elderly Patients with Nocturia, and the Correlation Between the Absorption of Desmopressin and Clinical Effect," BJU International, 95:804-809 (2005).

International Search Report and Written Opinion, PCT/IB2011/001010 dated Sep. 19, 2011.

International Search Report, EP Patent Application No. 03025959.2 dated May 10, 2004.

International Search Report, PCT/US2009/044860 dated Oct. 8, 2009.

International Search Report, GB Patent Application No. 0210387.6 dated Oct. 23, 2002.

International Search Report, PCT/EP07/001760 dated Sep. 11, 2007.

International Search Report, PCT/IB2003/02368, dated Mar. 19, 2004.

Irwin et al., "Population-based Survey of Urinary Incontinence, Overactive Bladder and Other Lower Urinary Ttract Symptoms in Ffive Countries: Results of the EPIC Study," Eur. Urol., 50:1306-1315 (2006).

Jahr et al., "Effect of Desmopressin Acetate on Hindlimb Perfusion Pressure in Rats: What is the Mechanism?," Anesthesia & Analgesia, 75(3):411-415 (1992).

Johnson et al., "Arginine Vasopressin and Nocturnal Polyuria in Older Adults with Ffrequent Nighttime Voiding" J. Urol, 170:480-484 (2003).

Jolleys et al., "Urinary Symptoms in the Community: How Bothersome Are They?" Br. J. Urol, 74:551-555 (1994).

(56) References Cited

OTHER PUBLICATIONS

Juul et al., "Gender Difference in Antidiuretic Response to Desmopressin," Am. J. Physiol. Renal. Physiol 300:F1116-F1122 (2011).
Kelleher et al., "Severe Hyponatremia Due to Desmopressin," The Journal of Emergency Medicine, 30(1):45-47 (2006).
Kikuchi, "Participation of Atrial Natriuretic Peptide (hANP) Levels and Arginine Vasopressin (AVP) in Aged Persons with Nocturia"; Japan J. Urol., 86:1651-1659 (1995).
Kirkland et al., "Patterns of Urine Flow and Electrolyte Excretion in Healthy Elderly People," British Medical Journal, 287:1665-1667 (1983).
Kobelt et al., "Productivity, Vitality and Utility in a Group of Professionally Active Individuals with Nocturia," BJU Int., 91:190-195 (2003).
Krishnamoorthy et al., "Prodrugs for Nasal Drug Delivery," Advanced Drug Delivery Review, 29:135-146 (1998).
Kuo, "Efficacy of Desmopressin in Treatment of Refractory Nocturia in Patients Older than 65 Years," Adult Urology, pp. 485-489, 2002.
Lackgren et al., "Desmopressin in the Treatment of Severe Nocturnal Enuresis in Adolescents—a 7-year Follow-up Study," British Journal of Urologym, 81(Suppl. 3):17-23 (1998).
Laczi et al., "Effects of Vasopressin Analogues (DDAVP, DVDAVP) in the Form of Sublingual Tablets in Central Diabetes Insipidus," International Journal of Clinical Pharmacology, Therapy and Toxicology, 18(12):63-68 (1980).
Lexner et al., "X-linked Hypohidrotic Ectodermal Dysplasia. Genetic and Dental Findings in 67 Danish Patients from 19 Families," Clin. Genet., 74:252-259 (2008).
Liu et al., "Gonadal Hormone Regulation of the Renal Vasopressin V2 Receptor," The FASEB Journal., 22:1159.24 (2008).
Liu et al., "Sex Differences in Vasopressin V2 Receptor Expression and Vasopressin-induced Antidiuresis," Am. J. Physiol. Renal. Physiol., 300:F433-F440 (2010).
Lose et al., "Clinical Experiences with Desmopressin for Long-term Treatment of Nocturia," The Journal of Urology, 172:1021-1025 (Sep. 2004).
Lose et al., "Efficacy of Desmopressin (Minirin) in the Treatment of Nocturia: A Double-blind Placebo-Controlled Study in Women," Am. J. Obstet. Gynecol., 189(4):1106-1113 (2003).
Lottmann et al., "A Randomised Comparison of Oral Desmopressin Lyophilisate (MELT) and Tablet Formulations in Children and Adolescents with Primary Nocturnal Enuresis," International Journal of Clinical Practice, 61(9):1454-1460 (2007).
Lundgren, "Nocturia: A New Perspective on an Old Symptom," Scand. J. Urol Nephrol, 38:112-116 (2004).
Malan et al., "Subcutaneous Administration of Desmopressin as a Test of Maximal Urinary Concentrating Ability in the Fischer 344 Rat," Toxicology Methods, 4(3):188-192 (1994).
Malmsten et al., "Urinary Incontinence and Lower Urinary Tract Symptoms: An Epidemiological Study of Men Aged 45 to 99 Years," J Urol, 158:1733-1737 (1997).
Manabe et al., "Sleep Patterns and Mortality Among Elderly Patients in a Geriatric Hospital," Gerontology, 46:318-322 (2000).
Matthiesen et al., "Nocturnal Polyuria and Natriuresis in Male Patients withNocturia and Lower Urinary Tract Symptoms," The Journal of Urology, 156:1292-1299 (1996).
Mattiasson et al., "Efficacy of Desmopressin in the Treatment of Nocturia: a Double-blind Placebo-controlled Study in Men," BJU International, 89:855-862 (2002).
Middelkoop, H. et al.; "Subjective sleep characteristics of 1,485 males and females aged 50-93: Effects of sex and age, and factors related to self-evaluated quality of sleep"; J Gerontol A Biol Sci Med Sci; 1996; vol. 51A; pp. M108-M115.
Migeon, X Inactivation, Female Mosaicism, and Sex Differences in Renal Diseases, J. Am. Soc. Nephrol., 19:2052-2059 (2008).
Miller et al., "Nocturnal Enuresis: Experience with Long-Term use of Intranasally Administered Desmopressin," The Journal of Pediatrics, 114(4)Part 2:723-726 (Apr. 1989).

Moon, D. et al.; "Antidiuretic hormone in elderly male patients with severe nocturia: a circadian study"; BJU Int 2004; vol. 94; pp. 571-575.
Natsume, O.; "A clinical investigation of nocturnal polyuria in patients with nocturia: A diurnal variation in arginine vasopressin secretion and its relevance to mean blood pressure"; J Urol; 2006; vol. 176; pp. 660-664.
Neveus et al, "The Standardization of Terminology of Lower Urinary Tract Function in Children and Adolescents: Report from the Standardisation Committee of the International Children's Continence Society," The Journal of Urology, 176:314-324 (Jul. 2006).
Neveus, "Nocturnal Enuresis—Theoretic Background and Practical Guidelines," Pediatr Nephrol, 26:1207-1214 (2011).
Norgaard et al., "Diurnal Anti-diuretic-Hormone Levels in Enuretics," Institute of Experimental Clinical Research, University of Aahus and Department of Medicine, Denmark, 134:1029-1031 (Nov. 1985).
Odeberg et al., "A Pharmacokinetic and Pharmacodynamic Study of Desmopressin: Evaluating Sex Differences and the Effect of Pre-Treatment with Piroxicam, and Further Validation of an Indirect Response Model," Journal of Pharmacy and Pharmacology, 56:1389-1398 (2004).
Office Action dated Aug. 2, 2011, U.S. Appl. No. 12/469,801.
Office Action dated Feb. 3, 2011, U.S. Appl. No. 12/469,801.
Office Action dated Feb. 8, 2013, U.S. Appl. No. 12/469,801.
Office Action dated Apr. 21, 2011, in co-pending U.S. Appl. No. 12/732,161.
Office Action dated Dec. 13, 2011, in co-pending U.S. Appl. No. 12/732,161.
Orstavik, "Skewed X Inactivation in Healthy Individuals and in Different Diseases," Acta Pediatrica, Suppl. 451:24-29 (2006).
Prevalence and Causes of Nocturia, pp. 441-446.
Rademaker, "Do Women Have More Adverse Drug Reactions?" Current Opinion, Am. J. Clin Dermatol, 2(6):349-351 (2001).
Ranchin et ali., "Familial Nephrogenic Syndrome of Inappropriate Antidiuresis: Dissociation between Aquaporin-2 and Vasopressin Excretion," The Journal of Clinical Endocrinology & Metabolism, 95(9):E37-E43 (Sep. 2010).
Rembratt et al., "Desmopressin Treatment in Nocturia an Analysis of Risk Factors for Hyponatremia," Neurology and Urodynamics, 25:105-209 (2006).
Remington: The Science and Practice of Pharmacy, vol. II, Mack Publishing Company, Easton, PA, 1995, Chapter 85, pp. 1492-1493.
Rittig et al., "Effect of Food Intake on the Pharmacokinetics and Antidiuretic Activity of Oral Desmopressin (DDAVP) in Hydrated Normal Subjects," Clinical Endocrinology, 48:235-241 (1998).
Rittig et al., "The Circadian Defect in Plasma Vasopressin and Urine Output is Related to Desmopressin Response and Enuresis Status in Children with Nocturnal Enuresis," 179:2389-2395 (Jun. 2008).
Rittig, "Basis and Therapeutical Rationale of the Urinary Concentrating Mechanism," Int. J. Clin. Pract., 61 (Suppl. 155):2-7 (2007).
Robertson, G.; "Nocturnal Polyuria"; BJU Int.; 1999; 84; Suppl. 1; pp. 17-19.
Roehrborn, "Definition of At-risk Patients: Baseline Variables," Journal Compilation, BJU International, 97(Suppl. 2):7-11 (2006).
Samuelsson, E et al.; "A population study of urinary incontinence and nocturia among women aged 20-59 years: Prevalence, well-being and wish for treatment"; Acta Obstet Gynecol Scan; 1997; vol. 76; pp. 74-80.
Sommer, P. et al.; "Voiding patterns and prevalence of incontinence in women: A questionnaire survey"; Br J Urol; 1990; vol. 66; pp. 12-15.
Sommer, P. et al.; "Voiding patterns in men evaluated using a questionnaire survey"; Br J Urol; 1990; vol. 65; pp. 155-160.
Stachenfeld et al., "Estrogen Effects on Osmotic Regulation of AVP and Fluid Balance," Am. J. Physiol. Endocrinol. Metab. 283:E711-E721 (2002).
Stachenfeld et al., "Estrogen Influences Osmotic Secretion of AVP and Body Water Blance in Postmenopausal Women," The American Physiological Society, R187-R195 (1998).
Stachenfeld et al., "Fluid Balance and Renal Response Following Dehydrating Exercise in Well-trained Men and Women," Eur. J. Appl. Physiol, 72:468-477 (1996).

(56) References Cited

OTHER PUBLICATIONS

Stachenfeld et al., "Genome and Hormones: Gender Differences in Physiology Selected Contribution: Sex Differences in Osmotic Regulation of AVP and Renal Sodium Handling," J. App. Physiol., 91:1893-1901 (2001).
Stewart, R. et al.; "Nocturia: A risk factor for falls in the elderly"; J Am Geriatr Soc; 1992; vol. 40; pp. 1217-1220.
Swithinbank, L. et al.; "A detailed description, by age, of lower urinary tractsymptoms in a group of community dwelling women"; BJU Int; 2000; 85 (suppl 2); pp. 19-24.
Tikkinen, K. et al.; "Is nocturia equally common among men and women? A population based study in Finland"; J Urol; 2006; vol. 175; pp. 596-600.
Tormey et al.; "Severe Prolonged Antidiuresis Following Desmopressin and Carbamazepine Interaction in Postoperative Diabetes Insipidus", European Journal of Internal Medicine, 1992, vol. 3, pp. 341-343.
Trinh-Trang-Tan et al. "Regulation of UT-A2 Protein in vivo and in vitro", Journal of the American Society of Nephrology, Program and Abstract Issue, Sep. 2000, vol. 11, pp. 23A.
Tubidy et al., "Long Term Use of Desmopressin for Urinary Symptoms in Multiple Sclerosis," Multiple Sclerosis, 5:416-417 (1999).
Van Dijk, L. et al.; "Nocturia in the Dutch adult population"; BJU Int; 2002; vol. 90; pp. 644-648.
Van Kerrebroeck et al., "The Standardization of Terminology in Nocturia: Report from the Standardization Sub-committee of the International Continence Society," Neurourol Urodunamics 21:179-183 (2002).
Van Kerrebroeck, P. et al.; "Desmopressin in the treatment of nocturia: A double-blind, placebo-controlled study"; Eur Uro; vol. 52; 2007; pp. 221-229.
Vande Walle et al., "A New Fast-melting Oral Formulation of Desmopressin: A Pharmacodynamic Study in Children With Primary Nocturnal Enuresis," BJU International, 97:603-609 (2006).
Vilhardt et al., "Plasma Kinetics of DDAVP in Man", Acta Pharmacol Toxicol, 1986, vol. 58, No. 5, pp. 379-381.
Vilhardt H.; "Basic pharmacology of desmopressin: A review"; Drug Invest; 1990; 2 (suppl 5); pp. 2-8.
Wagg, "Continence, Incontinence and the Aging Male," The Aging Male, 3:143-154 (2000).
Weiss et al., "Nocturia," The Journal of Urology, 163:5-12 (2000).
Weiss et al., "Desmopressin Orally Disintegrating Tablet Effectively Reduces Symptoms of Nocturia and Prolongs Undisturbed Sleep in Patients with Nocturia: Results of a Randomized Placebo-Controlled Study," 198-199.
Wolfson et al., "Mechanism of Vasopressin Inhibition of Pancreatic Secretion", American Journal of Gastroenterology, 71(5):490-495 (1979).
Zenenberg et al., "Hyponatremia Evaluation and Management," Hospital Practice, 38(1):89-96 (Feb. 2010).
Juul et al., "Long-Term Durability of Response to Desmopressin in Female and Male Nocturia Patients", Neurourology and Unodynamics (2013).
Notice of Third Party Opposition, filed in EP 09751584.5, Nov. 11, 2014 including Opponent data entitled "Comparison/Disintegration/Desmopressin Tablets."
Weiss et al., "Efficacy and Safety of Low Dose Desmopressin Orally Disintegrating Tablet in Men with Nocturia: Results of a Multi-center, Randomized, Double-Blind, Placebo Controlled, Parallel Group Study," The Journal of Urology, vol. 190, pp. 965-972, Sep. 2013.

METHODS COMPRISING DESMOPRESSIN

This application is a continuation of U.S. patent application Ser. No. 12/732,161 filed Mar. 25, 2010, which is a continuation-in-part of U.S. application Ser. No. 12/469,801, filed May 21, 2009, which claims the benefit of U.S. Provisional Application No. 61/055,120, filed May 21, 2008, the disclosures of which are incorporated herein by reference in their entireties.

Only recently has nocturia been recognized as a clinical entity in its own right as opposed to one of many symptoms comprising various lower urinary tract conditions. It is currently defined by the International Continence Society (ICS) as the complaint that the individual has to wake up at night one or more times to void. This applies to any number of voids at any time during the night provided the person is awake before voiding. (1) In general, the term nocturia refers to urination at night, especially when excessive. It is also referred to as "nycturia."

There are three broad categories of pathophysiology which account for nocturia: global polyuria; bladder storage problems; and nocturnal polyuria. (2)

Global polyuria is defined as urine output >40 ml/kg body weight during a 24 hour period. Causes of polyuria include diabetes mellitus, diabetes insipidus, and primary thirst disorders.

Bladder storage problems are characterized by frequent voids with small urine volumes. Causes of bladder storage problems include detrusor over activity (neurogenic and non-neurogenic); bladder hypersensitivity; bladder outlet obstruction; primary bladder pathology such as cystitis, calculi and neoplasia; and urogenital aging. A pattern of frequent waking and voiding is also characteristic of a primary sleep disturbance which should be part of the differential diagnosis in the evaluation of a patient with nocturia.

Nocturnal polyuria is defined as the production of an abnormally large volume of urine during sleep. Healthy young adults from 21-35 years of age excrete approximately 14±4% of their total urine between the hours of 11 p.m. and 7 a.m. whereas older people excrete an average of 34±15%. (3-4) The ICS currently defines nocturnal polyuria as a nocturnal urine volume greater than 20-30% of total 24 hour urine volume, depending on age and in the absence of polyuria. (5)

Nocturnal polyuria may be secondary to systemic conditions such as congestive heart failure, peripheral edema due to venous stasis or lymphostasis, renal or hepatic failure, lifestyle patterns such as excessive nighttime drinking, and obstructive sleep apnea. Several studies suggest that some individuals with nocturia may have a loss of the normal circadian rhythmicity of arginine vasopressin (AVP) secretion. (6-12) AVP is the hormone primarily responsible for the regulation of urine production. In healthy adults, there is a diurnal release of AVP with peak blood concentrations occurring during the hours of sleep. (13) Blunting of the nocturnal phase of AVP secretion in subjects with nocturia would provide one plausible physiologic explanation for increased nocturnal urine production. However, not all patients with nocturia lack circadian AVP variation, and not all patients lacking circadian AVP variation have nocturia. (14) There are multiple physiologic changes in the mechanisms governing water and sodium regulation which can alter the diurnal rhythm of urine excretion. These include age-related declines in renal concentrating ability and plasma renin concentrations. (15)

Estimates of nocturia prevalence vary widely depending on the definition used, analytical method employed and population and region surveyed. (16-28) Despite these limitations, the literature strongly indicates that nocturia is a common and bothersome condition in males and females that increases in both prevalence and severity with age.

One recent large survey, involving more than 19,000 males and females age 18 and older in five countries (Canada, Germany, Italy, Sweden, and the United Kingdom) and utilizing the ICS definition of nocturia (one or more times per night) showed that nocturia was the most prevalent lower urinary tract symptom—reported by 48.6% of men and 54.5% of women—and increased from 34-44% in individuals less than 39 years old to over 70% in those aged 60 years or more. Even with a higher threshold of two or more voids per night, the nocturia prevalence of 21-24% exceeded that of any other lower urinary tract symptom. (29)

Older adults often cite nocturia as one of the most bothersome lower urinary tract symptoms. In a community-based survey of 423 men age 40 and older in the UK, 58 (14%) reported nocturia at least twice per night. And 67% of these reported that it was "at least a bit of a problem"—the second most bothersome symptom after frequency at least 9 times per day (92%), and more bothersome even than nocturnal incontinence (60%). (30) A community-based survey conducted in the USA including 720 subjects with nocturia showed that as little as one void per night was not only bothersome, but negatively affected health-related quality of life and sleep. For respondents with nocturia ≥2 times per night, the impact on health related quality of life was similar to that of type 2 diabetes and greater than that of hypertension. (31)

The most pernicious effect of nocturia is not excessive voiding per se, but its impact on sleep quality and subsequent daytime function as a consequence of sleep disruption. There is a well established relationship between nocturia and sleep quality. A community-based Dutch survey of 1485 people age 50 and older reported that 25.3% reported disturbed sleep maintenance, for which nocturia was the most frequent cause (67.5%). (32)

Asplund and Aberg investigated the relationship between sleep and nocturia in a sample of 3000 women and found that sleep deteriorated in association with increased nighttime voiding. Women with 3 or more voids per night reported four times more often that they lacked sleep and suffered from daytime sleepiness. (33)

Insufficient sleep and daytime fatigue have been linked with depression, mood alteration and diminished quality of life. (34-36) A community-based Swedish survey of 203 working individuals with nocturia and 80 randomly selected controls showed that the group with nocturia had significantly lower levels of vitality and utility and greater impairment of work and activity as a consequence of sleep deprivation. (37)

Nocturia is also associated with an increased incidence of falls during the nighttime hours. (38) Falls are a major health problem among older persons and are the leading cause of death from injuries in this age group. (39) In a study evaluating the risk of falls in ambulatory patients 65 years of age and older with nocturia, the odds ratio for falling increased from 1.46 for subjects with one nocturia event to 2.15 for subjects reporting more than three nocturia events per night. (40)

Vasopressin is the primary physiologic determinant of free water excretion. It increases the water permeability of the luminal membrane of the renal cortical and medullary collecting ducts thereby promoting free water reabsorption and reducing urine production. As nocturia is the clinical consequence of excess nocturnal urine production relative to bladder capacity, reduction of nocturnal urine volume should logically result in fewer nighttime voiding episodes.

Desmopressin is a synthetic analogue of the naturally occurring hormone 8-arginine vasopressin, with modifications including deamination of 1-cysteine and substitution of L-arginine at position 8 by D-arginine. Desmopressin exhibits a high and specific antidiuretic effect as disclosed in U.S. Pat. No. 3,497,491. The resulting molecule has an antidiuretic-to-vasopressor ratio 3000-fold greater than vasopressin and a longer duration of action. (41)

Due to the bothersome nature and varied symptoms associated with nocturia, further investigation of desmopressin was warranted. Those investigations examined the efficacy and safety of desmopressin in broad populations. The result was surprising gender, age, and dose effects of desmopressin.

SUMMARY

The present disclosure is directed to gender, age, and dose effects of desmopressin on reducing nocturnal voids, increasing an initial period of undisturbed sleep, and/or reducing nocturnal urine volume.

For example, the present disclosure provides a method for increasing an initial period of undisturbed sleep in a patient in need thereof comprising: administering to the patient prior to bedtime an orodispersible dose of desmopressin of 10 μg, wherein the dose is measured as the free base of desmopressin and the dose taken over a treatment period increases the patient's initial period of undisturbed sleep.

In further embodiments, the present disclosure is directed to a method for reducing nocturnal urine volume in a patient in need thereof comprising: administering to the patient prior to bedtime an orodispersible dose of desmopressin of 10 μg, wherein the dose is measured as the free base of desmopressin and the dose taken over a treatment period reduces the patient's nocturnal urine volume.

In still further embodiments, the present disclosure provides a method for reducing nocturnal voids in a female patient in need thereof comprising: administering to the patient prior to bedtime an orodispersible dose of desmopressin of 10 μg or 25 μg, wherein the dose is measured as the free base of desmopressin and the dose taken over a treatment period reduces the patient's nocturnal voids.

In other embodiments, the present disclosure is directed to a method for increasing an initial period of undisturbed sleep in a female patient in need thereof comprising: administering to the patient prior to bedtime an orodispersible dose of desmopressin of 10 μg or 25 μg, wherein the dose is measured as the free base of desmopressin and the dose taken over a treatment period increases the patient's initial period of undisturbed sleep.

In yet further embodiments, the present disclosure provides a method for reducing nocturnal urine volume in a female patient in need thereof comprising: administering to the patient prior to bedtime an orodispersible dose of desmopressin of 10 μg or 25 μg, wherein the dose is measured as the free base of desmopressin and the dose taken over a treatment period reduces the patient's nocturnal urine volume.

Further for example, the present disclosure is directed to a method for reducing nocturnal voids in a female patient above 50 years of age in need thereof comprising: administering to the patient prior to bedtime an orodispersible dose of desmopressin of 10 μg or 25 μg, wherein the dose is measured as the free base of desmopressin and the dose taken over a treatment period reduces the patient's nocturnal voids.

In still further embodiments, the present disclosure provides a method for increasing an initial period of undisturbed sleep in a female patient above 50 years of age in need thereof comprising: administering to the patient prior to bedtime an orodispersible dose of desmopressin of 10 μg or 25 μg, wherein the dose is measured as the free base of desmopressin and the dose taken over a treatment period increases the patient's initial period of undisturbed sleep.

In yet further embodiments, the present disclosure is directed to a method for reducing nocturnal urine volume in a female patient above 50 years of age in need thereof comprising: administering to the patient prior to bedtime an orodispersible dose of desmopressin of 10 μg or 25 μg, wherein the dose is measured as the free base of desmopressin and the dose taken over a treatment period reduces the patient's nocturnal urine volume.

In other useful embodiments, the present disclosure provides a method for reducing nocturnal voids in a female patient above 65 years of age in need thereof comprising: administering to the patient prior to bedtime an orodispersible dose of desmopressin of 25 μg, wherein the dose is measured as the free base of desmopressin and the dose taken over a treatment period reduces the patient's nocturnal voids.

In further useful embodiments, the present disclosure is directed to a method for increasing an initial period of undisturbed sleep in a female patient above 65 years of age in need thereof comprising: administering to the patient prior to bedtime an orodispersible dose of desmopressin of 25 μg, wherein the dose is measured as the free base of desmopressin and the dose taken over a treatment period increases the patient's initial period of undisturbed sleep.

In particular embodiments, the present disclosure provides a method for reducing nocturnal urine volume in a female patient above 65 years of age in need thereof comprising: administering to the patient prior to bedtime an orodispersible dose of desmopressin of 25 μg, wherein the dose is measured as the free base of desmopressin and the dose taken over a treatment period reduces the patient's nocturnal urine volume.

In some embodiments, the present disclosure is directed to a method for reducing nocturnal urine volume in a male patient in need thereof comprising: measuring the patient's serum sodium level; administering to the patient, with a serum sodium level of at least 130 mmol/L, prior to bedtime an orodispersible dose of desmopressin of 100 μg, wherein the dose is measured as the free base of desmopressin; measuring the patient's serum sodium level at a time interval after administration; continuing the administration of the dose of desmopressin with the patient having at least 130 mmol/L serum sodium level; wherein the dose administered over a treatment period reduces the patient's nocturnal urine volume.

In another embodiment, the disclosure provides a method of treating nocturia by administering to a subject in need thereof a sublingual daily dose of about 10 μg, 25 μg, 50 μg, or 100 μg desmopressin (measured as the free base). The subject to be treated has an average of a least 0.5 fewer nocturnal urinary voids per night after 28 days of treatment with desmopressin.

In a further embodiment, the present disclosure is directed to a method for reducing nocturnal voids in a patient in need thereof comprising: administering to the patient prior to bedtime an orodispersible dose of desmopressin ranging from 25 µg to 100 µg, wherein the dose is measured as the free base of desmopressin and the dose taken over a minimum treatment period reduces the patient's nocturnal voids compared to the patient's nocturnal voids before administration of the dose.

In still yet another embodiment, the present disclosure provides for a method for improving a reduction in nocturnal voids in a patient in need thereof comprising: administering to the patient prior to bedtime an orodispersible dose of desmopressin ranging from 25 µg to 100 µg, wherein the dose is measured as the free base of desmopressin and the dose taken over a minimum treatment period reduces the patient's nocturnal voids compared to before administration and improves the reduction in nocturnal voids over the duration of the minimum treatment period.

In a further embodiment, the present disclosure provides for a method for maintaining a reduction in nocturnal voids in a patient in need thereof comprising: administering to the patient prior to bedtime an orodispersible dose of desmopressin of ranging from 25 µg to 100 µg, wherein the dose is measured as the free base of desmopressin and the dose is taken over a minimum treatment period reduces the patient's nocturnal voids compared to the patient's nocturnal voids before administration of the dose.

DESCRIPTION

Figure 1:
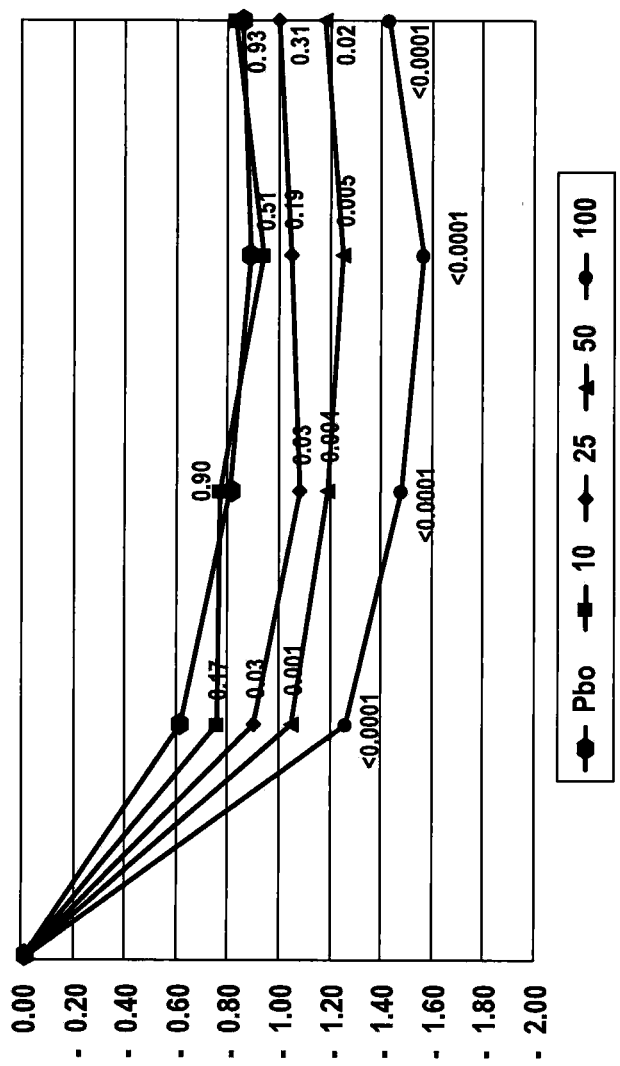
FIG. 1 graphically illustrates the weekly change from baseline in mean number of nocturnal voids along with the corresponding p-values.

Particular aspects of the disclosure are described in greater detail below. The terms and definitions as used in the present application and as clarified herein are intended to represent the meaning within the present disclosure. The patent and scientific literature referred to herein and referenced above are hereby incorporated by reference. The terms and definitions provided herein control, if in conflict with terms and/or definitions incorporated by reference.

Terms and Definitions

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency or value. With regard to specific values, it should be understood that specific values described herein for subject populations (e.g., the subject of the described clinical trial) represent median values, unless otherwise indicated as, e.g., mean values. Accordingly, aspects of the present disclosure requiring a particular value in a subject are substantially supported herein by population data in which the relevant value is assessed to be a meaningful delimitation of the subject population.

As used herein, the term "first sleep period" refers to the time elapsed from bedtime to either first void or morning arising.

The term "hyponatraemia" as used herein refers to a serum sodium value below the lower limit of the normal reference range, for example, a serum sodium level <130 mmol/L.

The term "nocturnal enuresis" as used herein refers to a condition in which a person who has bladder control while awake urinates while asleep.

As used herein, the term "nocturnal polyuria" refers to an increased nocturnal output of urine. For example, a ratio of nighttime urine volume over the 24-hour urine volume to be equal to or greater than 33%.

As used herein, the term "nocturnal urine" refers to the total urine volume from 5 minutes after bedtime until rising in the morning, including the first void within 30 minutes of rising.

The term "nocturnal void" as used herein refers to a void occurring from 5 minutes after bedtime until rising in the morning with the intention of getting up.

The term "nocturia" refers to the complaint that an individual has to wake up at night one or more times to void.

The term "overactive bladder" as used herein refers to urgency, with or without urge incontinence, usually accompanied by frequency and nocturia.

The term "polydipsia" as used herein refers to excessive fluid consumption.

The term "urine osmolaity" as used herein refers to the concentration of electrolytes in urine.

The term "uroflometry" as used herein refers to a measurement of the rate of urine expelled from the bladder during bladder emptying. Flow rate is measured as mL/sec voided.

The terms "administer," "administration" or "administering" as used herein refer to (1) providing, giving, dosing and/or prescribing by either a health practitioner or his authorized agent or under his direction desmopressin, and (2) putting into, taking or consuming by the patient or person himself or herself, desmopressin.

LIST OF ABBREVIATIONS

Abbreviations Meaning of Abbreviations in Document
AE Adverse Event
ITT Intention-To-Treat
LOCF Last-Observation-Carried-Forward
MED Minimum Effective Dose
OC Observed Cases
PP Per Protocol
SD Standard Deviation
SAE Serious Adverse Event
NQoL Nocturia Quality of Life Questionnaire
PSQI Pittsburgh Sleep Quality Index
SF Short Form
µg Microgram
WebEZ Web Based Centralized Patient Randomization System
Melt Formulation Desmopressin Melt tablets contain desmopressin acetate in a freeze-dried presentation formulated with fish gelatin, mannitol and citric acid. The resulting oral lyophilisate disintegrates instantaneously in the mouth without the need for water. An orodispersible pharmaceutical dosage form of desmopressin with good bioavailability is described in U.S. patent application Ser. No. 10/513,437 (U.S. Pub. No. 2005/0232997 A1), the contents of which are incorporated herein in their entirety. The Melt dosage form is preferably provided as a desmopressin acetate salt. The desmopressin dosage may be expressed as free base, even though the desmopressin is actually supplied as the acetate salt. Except where otherwise indicated, the doses utilized in the present methods correspond to desmopressin free base even though the dosage form is a desmopressin acetate. Therefore, the 100 μg dose of desmopressin described herein is 100 μg of desmopressin free base, which corresponds to a proportionately higher weight value of desmopressin acetate (approximately 112.4 μg of desmopressin acetate for a desmopressin Melt preparation that is 89% w/w of desmopressin free base and for which the balance of 11% w/w is acetate, water and impurities). Similarly, the 50 μg, 25 μg, and 10 μg dosages all represent the weights of desmopressin free base, with the corresponding weights of desmopressin acetate being proportionately higher. Accordingly, 0.1 mg of desmopressin acetate is equivalent to about 89 μg of desmopressin free base.

The relative bioavailability between the tablet and melt formulations was investigated in an open-label, randomized crossover study in which 28 healthy subjects were administered 240 μg melt and 0.4 mg tablet (given as 2×0.2 mg tablets) separated by seven days. AUC, $C_{max}$, $T_{max}$ and $t_{1/2}$ were similar, indicating that 0.1 mg tablet results in exposure similar to that of a 60 μg melt (equivalent to 67 μg of desmopressin acetate).

Example: Clinical Study

Objectives

The primary objectives of Part I of this study (28-day efficacy) were: (1) to demonstrate the superiority of one or more doses of the Melt formulation of desmopressin to placebo in reducing the mean number of nocturnal voids in a broad population of adult patients with nocturia after 28 days of treatment; (2) to demonstrate the superiority of one or more doses of the Melt formulation of desmopressin to placebo in the proportion of subjects with >33% reduction from baseline in mean number of nocturnal voids after 28 days of treatment; and (3) treatment safety.

The primary objectives of Part II of this study (extension study) were: (1) to demonstrate the durability of effect achieved in Part I of one or more doses of desmopressin Melt; and (2) treatment safety.

The secondary objective of both Parts I and II was: to compare the effect of several doses of desmopressin Melt to placebo o sleep disturbance and quality of life.

Overall Study Design

This was a 2-part (Parts I and II), randomized, double-blind, placebo-controlled, parallel-group, multicenter study to investigate the efficacy and safety of 4 doses of a fast-dissolving ("Melt") formulation of desmopressin for the treatment of nocturia in adults. All treatments were administered orally once per night approximately 1 hour prior to bedtime; subjects were instructed to limit their fluid intake prior to drug self-administration. In Part I, subjects were randomly assigned to 1 of 5 treatment groups: placebo or desmopressin Melt 10 μg, 25 μg, 50 μg, or 100 μg. Randomization was to be stratified by age (<65, ≥65 years) and by the absence/presence of nocturnal polyuria, defined as a ratio of nighttime urine volume/24-hour urine volume ≥33%. To achieve the desired number of subjects within each stratum, enrollment of subjects in a particular stratum (age and/or presence/absence of nocturnal polyuria) could be halted. If this was necessary, all investigative sites were to be informed in writing at least 1 week in advance to stop screening in a population of subjects.

A total of 750 subjects were planned to be enrolled, with approximately 150 subjects per treatment group. Part I of the study was conducted in 7 visits. Screening (Visit 1) occurred within 21 days of dosing (Day 1, Visit 2); subjects returned for follow-up visits on Days 4, 8, 15, 22, and 28 (end of Part I). Duration of treatment in Part I was 28 days.

Immediately upon completion of Part I of the study, all subjects on active treatment continued into Part II on the same treatment for approximately 1 to 6 months. Subjects assigned to placebo in Part I were randomly assigned to 1 of the 4 active treatments in Part II. To ensure that the study remained fully blinded during the full extent of both Parts I and II, re-randomization of subjects assigned to placebo after 4 weeks of treatment was predetermined at the time of initial randomization.

Subjects began Part II at the Final Visit for Part I (Day 28) and returned for follow-up visits on Days 4, 8, 15, 29, and every 4 weeks thereafter until the database was locked for Part I and the treatment groups were unblinded. The total treatment duration for each subject depended on when that subject was randomized in Part I and was estimated to be a minimum of 4 weeks and a maximum of 6 months.

Upon completion of Part II of the study, subjects were given the option to participate in an open-label study with expected total treatment duration (double-blind extension plus open-label study) of at least 12 months (i.e., Part III). In Part III, subjects were assigned to the same treatment as in Part II, initially in a blinded manner. Subjects were unblinded and the study became open label only when all subjects in Parts I and II remaining in the study had entered Part III. During Part III, 10 μg was identified as a subtherapeutic dose based on efficacy data from Part I. As a consequence, patients in the 10 μg treatment group were re-randomized (beginning Q4 2008) to one of the other treatment groups (i.e., 25 μg, 50 μg, or 100 μg). The total treatment duration was at least 12 months.

A total of 508 patients entered the open-labeled extension (i.e., Part III). In total, 367 patients had ≥1 year of treatment.

Selection of Doses in Study

A previous clinical program investigating the efficacy and safety of a Tablet formulation of desmopressin for nocturia utilized doses of 100 μg, 200 μg, and 400 μg. All 3 doses demonstrated a clear effect on pharmacodynamic and clinical endpoints. Although the use of a dose-titration scheme limits the interpretation of dose response, doses higher than 100 μg offered only a marginal improvement in efficacy.

The dose relationship between the Tablet and Melt formulations was investigated in an open-label, randomized crossover study in which 28 healthy subjects were administered 240 μg Melt and 400 μg Tablet (given as 2×200 μg Tablets) separated by 7 days. AUC, $C_{max}$, $T_{max}$, and $t_{1/2}$ were similar, indicating that 100 μg Tablet provides an exposure similar to that of 60 μg Melt.

The present study investigated dose levels substantially lower than those used in the Tablet study. While there are no data with the Melt formulation in the target population to guide dose selection for doses below 100 μg tablet/60 μg Melt, pharmacokinetic (PK) and pharmacodynamic (PD) studies have been conducted in water-loaded healthy subjects and water-loaded children 6 to 12 years of age with nocturnal enuresis. Based on data from these 2 studies, a model simulating PK and PD has been developed. If antidiuretic activity is defined in terms of duration of urine osmolality greater than 200 mOsm/kg, the model indicates that a dose of 10 μg Melt may potentially be subtherapeutic and doses of 25 μg to 100 μg should provide 2.75 to 8.5 hours of antidiuretic activity.

Selection of Study Population: Inclusion Criteria

Subjects who met the following inclusion criteria were eligible for the study: provided written informed consent prior to the performance of any study-related activity, defined as any procedure that would not have been performed during the normal management of the subject; and was a male or female subject, 18 years of age and older, with an average of ≥2 nocturnal voids per night determined via a 3-day frequency-volume chart during the screening period Exclusion Criteria The presence of any of the following excluded a subject from study enrollment:

Genitourinary Tract Conditions

Males:

Clinical suspicion of bladder outlet obstruction and/or urine flow <5 mL/sec. If medical history and/or physical examination suggested bladder outlet obstruction, uroflowmetry was to be performed to confirm the diagnosis.

Surgical treatment, including transurethral ablative treatments, for bladder outlet obstruction/benign prostatic hyperplasia (BPH) performed within the past 6 months.

Females:

Pregnancy; females of reproductive age were to document they were using a reliable method of contraception.

Use of pessary for pelvic prolapse.

Presence of unexplained pelvic mass.

Males and Females:

Clinical suspicion of urinary retention and/or post-void residual volume >150 mL; if medical history and/or physical examination suggested urinary retention, bladder ultrasound or catheterization was to be performed to confirm the diagnosis.

Current or past urologic malignancies (e.g., bladder cancer, prostate cancer).

Clinical evidence of current genitourinary tract pathology that could interfere with voiding.

History of neurogenic detrusor activity (previously known as detrusor hyperreflexia).

Systemic Medical Conditions

Suspicion or evidence of cardiac failure.

Uncontrolled hypertension.

Uncontrolled diabetes mellitus.

Renal insufficiency; serum creatinine was to be within normal limits and estimated glomerular filtration rate (eGFR) was to be ≥60 mL/min.

Hepatic and/or biliary disease; aspartate transaminase (AST) and/or alanine transaminase (ALT) were not to be >2×upper limit of normal (ULN) and total bilirubin was not to be >1.5 mg/dL.

Hyponatraemia; serum sodium level was to be within normal limits as defined by the Sponsor and central laboratory.

Diabetes insipidus (urine output >40 mL/kg over 24 hours).

Syndrome of inappropriate antidiuretic hormone secretion (SIADH).

Psychogenic or habitual polydipsia.

Obstructive sleep apnea requiring therapy.

Other

Known alcohol or substance abuse.

Work or lifestyle that potentially interfered with regular nighttime sleep (e.g., shift workers).

Previous desmopressin treatment for nocturia.

Any other medical condition, laboratory abnormality, psychiatric condition, mental incapacity, or language barrier that, in the judgment of the Investigator, rendered the subject unsuitable for a clinical trial or impaired subject participation in the study.

Use of loop diuretics (furosemide, torsemide, ethacrynic acid). Other classes of diuretics (thiazides, triamterene, chlorthalidone, amiloride, indapamide) were permitted, either as monotherapy or combination therapy. Subjects using a diuretic were to be encouraged to take it in the morning, if medically feasible.

Use of any other investigational drug within 30 days of screening.

Discontinuation Criteria

Any subject with a serum sodium value of 125 mmol/L or less at any point during the study was to be withdrawn immediately and further evaluated and treated as necessary.

Subjects had the right to withdraw from the study at any time for any reason without providing justification. However, the Investigator was to take appropriate steps to ensure that withdrawal was accomplished in a safe manner. A subject could also be discontinued at the discretion of the Investigator or Sponsor because of safety concerns or if judged noncompliant with the study procedures to an extent that could affect the study results. The Investigator and the Sponsor were to agree on subject discontinuation prior to withdrawal, and unnecessary withdrawal of subjects was to be avoided.

Subjects discontinued from the study were to be scheduled for an End-of-Study (EoS) assessment as soon as possible after the decision to withdraw the subject had been made. For any discontinuation, the Investigator was to obtain all the required data and document the date of the premature withdrawal and the main reason in the electronic case report form (eCRF). If the reason for withdrawal was an adverse event (AE), the specific event or laboratory abnormality was to be recorded in the eCRF. The Investigator was to make a thorough effort to document the outcome. Discontinued subjects were not replaced.

Treatments Administered

Study drug was administered as an orally disintegrating tablet of desmopressin (desmopressin Melt) or placebo.

Subjects were randomly assigned to 1 of 5 fixed-dose treatment groups in Part I: placebo or desmopressin Melt 10 μg, 25 μg, 50 μg, or 100 μg. All treatments were administered orally once per night approximately 1 hour prior to bedtime. Subjects were instructed to place the tablet under their tongue, without water. Subjects were provided with sufficient study drug for the duration of Part I.

Study Endpoints

The primary endpoints for efficacy assessment were: (1) change in mean number of nocturnal voids from baseline evaluation to final visit (Day 28); and (2) proportion of subjects with >33% reduction in the mean number of nocturnal voids from baseline to final visit (Day 28). A further description and corresponding data directed to the second primary endpoint (i.e., portion of subjects with >33% reduction in the mean number of nocturnal voids) are not provided herein.

The secondary efficacy endpoints were: (1) durability of effect achieved in Part I; (2) change in initial period of undisturbed sleep, defined as the elapsed time in minutes from going to bed with the intention of sleeping to the time of awakening for the first nocturnal void; and (3) change in duration of total sleep time. Additional secondary endpoints were collected, e.g., change in nocturia-specific quality of life as assessed by scores on the International Consultation on Incontinence Modular Questionnaire—Noctuira and the Noctuira Quality of Life Questionnaire, change in quality of sleep as assessed by the global score of the Pittsburgh Sleep Quality Index, and change in overall quality of life as assessed by the short form-12v2. A description of the additional secondary efficacy endpoints and their accompanying data are not provided herein.

Changes in urine volume from baseline to the end of Day 28 were also assessed and included herein.

Flow Chart

A study flow chart, showing study assessments and procedures conducted at each study visit, are presented in Table 1 for Part I.

for discontinuation overall were withdrawal of consent (4%), adverse event (2%), and lost to follow-up (2%).

Data Sets Analyzed

Of the 799 randomized subjects in Part I, 757 subjects who received at least 1 dose of study drug and had follow-up data were included in the intent to treat (ITT) analysis dataset. Overall, 10% of ITT subjects had a major protocol violation and were excluded from the per-protocol (PP)

TABLE 1

Study flow chart for Part I.

| | Visit | | | | | | |
|---|---|---|---|---|---|---|---|
| | (screening) 1 | (randomization) 2 | 3 | 4 | 5 | 6 | 7 (EoS)[a] |
| | | | Week | | | | |
| Procedure | ≤21 days of Visit 2 | 1 | 1 4 | 2 8 | 3 15 ± 3 | 4 22 ± 3 | 4 28 ± 3 |
| Informed consent | X[b] | | | | | | |
| Inclusion/exclusion criteria | X | | | | | | |
| Login to WebEZ for Subject ID number | X | | | | | | |
| Demographic/medical history | X | | | | | | |
| Body weight | X | | | | | | X |
| Height | X | | | | | | |
| Physical examination | X | | | | | | X |
| Vital signs (BP, pulse) | X | X | X | X | X | X | X |
| Concomitant medications | X | X | X | X | X | X | X |
| Labs: chemistry (including serum sodium), hematology, urinalysis | X | | | | | | X |
| Urine osmolality[c] (exploratory) | X | | | | | | |
| Urine pregnancy test | X | | | | | | X |
| Uroflometry (males only)[d] | X | | | | | | |
| Assess post void residual volume[d] | X | | | | | | |
| Dispense sleep/voiding diary (3 days)[e] | X | | | | | X | |
| Actigraphy[f] | X | | | | | X | |
| Adverse events | | X | X | X | X | X | X |
| Review voiding and/or sleep diary | | X | | X | X | X | X |
| Nocturia questionnaires: ICIQ-N, PSQI, NQoL, SF-12v2 | | X | | | | | X |
| Randomization via WebEZ | | X | | | | | |
| Dispense voiding diary (3 days)[e] | | | X | X | X | | |
| Serum sodium | | | X | X | X | X | |
| Study drug accountability | | | X | X | X | X | X |
| Dispense study drug for Part II (kit number assigned via WebEZ) | | | | | | | X |

EoS = End of Study;
WebEZ = web-based centralized patient randomization system;
BP = blood pressure;
ICIQ-N = International Consultation on Incontinence questionnaire - Nocturia;
PSQI = Pittsburgh Sleep Quality Index;
NQoL = Nocturia Quality of Life;
SF-12v2 = Short Form-12, version 2
[a]Discontinued subjects were to complete an End-of-Study Visit as soon as possible after study discontinuation.
[b]Written informed consent was to be obtained prior to any study-related procedures.
[c]Collection of first night-time urine void prior to randomization visit.
[d]Uroflometry was collected in males only if there was suspicion of obstruction; post residual urine volume was measured using an ultrasound only if there was clinical suspicion of urinary retention.
[e]Voiding diaries were completed for 3 consecutive 24-hour cycles; diaries for Weeks 1, 2, and 3 only required the "wake time" of the night-time void.
[f]Actigraphy was used in a subset of subjects (at 6 study sites).

Disposition of Subjects

A total of 1412 subjects were screened for Part I of the study; 613 subjects were screening failures and 799 subjects were randomized to treatment. The most common recorded reasons for screening failure were renal insufficiency (15%) and not averaging ≥2 nocturnal voids over the 3-day screening period (10%). A total of 710 (89%) subjects completed Part I of the study and 89 (11%) subjects prematurely discontinued. Across treatment groups, 6% to 16% of subjects prematurely discontinued. The most common reasons analysis dataset. Of the 682 PP subjects, 10% did not have both screening and final visit data on number of nocturnal voids and were excluded from the observed cases (OC) analysis dataset. All 799 randomized subjects received at least 1 dose of study drug (desmopressin or placebo) and had at least 1 safety assessment and, therefore, were included in the safety analysis dataset.

Primary Efficacy Endpoint

Number of Nocturnal Voids

The mean number of nocturnal voids decreased from baseline to Day 28 in all treatment groups, with greater decreases observed with increasing dose of desmopressin.

The reduction in mean number of nocturnal voids, compared to placebo, was statistically significant for the 100 µg (p<0.0001) and 50 µg (p=0.0207) groups.

The trend of greater decreases in mean number of nocturnal voids with increasing dose of desmopressin was evident in subjects stratified by age (<65 years, ≥65 years) and in subjects with nocturnal polyuria. Too few subjects (13 to 18 subjects per treatment group) did not have nocturnal polyuria to make meaningful comparisons. The reduction in mean number of nocturnal voids, compared to placebo, was statistically significant for the 100 µg group for all 4 stratification factors and for the 50 µg group for subjects with nocturnal polyuria.

A summary of changes from baseline to the final visit in the number of nocturnal voids is presented for all groups (ITT population) in Table 2.

TABLE 2

Change from baseline to final visit (Day 28) of nocturnal voids (ITT analysis dataset in Part I) for all groups.

| Dose | n | mean | stddev | stderr | min | median | max |
|---|---|---|---|---|---|---|---|
| Placebo | 156 | −0.86 | 1.05 | 0.08 | −4.00 | −0.83 | 1.67 |
| 10 ug | 155 | −0.83 | 1.07 | 0.09 | −4.33 | −0.67 | 2.33 |
| 25 ug | 152 | −1.00 | 1.13 | 0.09 | −3.67 | −1.00 | 2.33 |
| 50 ug | 148 | −1.18 | 1.19 | 0.10 | −5.00 | −1.00 | 2.00 |
| 100 ug | 146 | −1.43 | 1.22 | 0.10 | −5.00 | −1.33 | 4.33 |
| Total | 757 | −1.05 | 1.15 | 0.04 | −5.00 | −1.00 | 4.33 | n—population size; stddev—standard deviation; stderr—standard error; min—minimum; and max—maximum Mean decreases in the number of nocturnal voids were observed by Day 8, with a trend for greater decreases with increasing desmopressin doses; these findings continued at Day 15 and Day 22. Notably, compared to placebo, statistically significant differences were observed for the 25 µg, 50 µg, and 100 µg doses on Day 8 and Day 15 of treatment, with significant differences for the 2 higher doses also on Day 22 and Day 28. Weekly change from baseline in mean number of nocturnal voids, along with p-values for each desmopressin Melt dose compared to placebo, is displayed in FIG. 1.

Among females, the reduction in mean number of nocturnal voids, compared to placebo, was statistically significant for the 100 µg (p<0.0001), 50 µg (p=0.0091), and 25 µg (p=0.0200) groups. Thus, among females, efficacy was demonstrated for the primary endpoint of nocturnal voids for all but the lowest dose of desmopressin.

A summary of changes from baseline to the final visit in the number of nocturnal voids is presented for all females, females over 50 years of age, and females over 65 years of age (ITT population) in Tables 3, 4 and 5.

TABLE 3

Change from baseline to final visit (Day 28) of nocturnal voids (ITT analysis dataset in Part I) for all females.

| Dose | n | mean | stddev | stderr | min | median | max |
|---|---|---|---|---|---|---|---|
| Placebo | 66 | −0.88 | 1.01 | 0.12 | −3.33 | −0.67 | 1.00 |
| 10 ug | 73 | −1.15 | 1.07 | 0.13 | −4.33 | −1.00 | 1.00 |
| 25 ug | 65 | −1.22 | 1.06 | 0.13 | −3.33 | −1.33 | 1.00 |
| 50 ug | 71 | −1.23 | 1.06 | 0.13 | −4.00 | −1.00 | 2.00 |
| 100 ug | 66 | −1.51 | 1.14 | 0.14 | −5.00 | −1.33 | 1.00 |
| Total | 341 | −1.20 | 1.08 | 0.06 | −5.00 | −1.00 | 2.00 | n—population size; stddev—standard deviation; stderr—standard error; min—minimum; and max—maximum Although not statistically significant for the 10 µg group but statistically significant for the 25 µg group, there was a decrease observed in the median number of nocturnal voids identified in Table 3 for all females. For example, the 10 µg and 25 µg groups exhibited at least 1.0 fewer nocturnal urinary voids per night on desmopression treatment compared to baseline before treatment. The placebo exhibited only 0.67 fewer nocturnal urinary voids per night compared to baseline.

TABLE 4

Change from baseline to final visit (Day 28) of nocturnal voids (ITT analysis dataset in Part I) for females over 50 years of age.

| Dose | n | mean | stddev | stderr | min | median | max |
|---|---|---|---|---|---|---|---|
| Placebo | 45 | −0.74 | 0.93 | 0.14 | −2.67 | −0.67 | 1.00 |
| 10 ug | 51 | −1.08 | 1.04 | 0.15 | −4.33 | −1.00 | 0.33 |
| 25 ug | 49 | −1.35 | 1.04 | 0.15 | −3.33 | −1.33 | 1.00 |
| 50 ug | 55 | −1.15 | 1.13 | 0.15 | −4.00 | −1.00 | 2.00 |
| 100 ug | 48 | −1.44 | 1.24 | 0.18 | −5.00 | −1.33 | 1.00 |
| Total | 248 | −1.16 | 1.10 | 0.07 | −5.00 | −1.00 | 2.00 | n—population size; stddev—standard deviation; stderr—standard error; min—minimum; and max—maximum Although not statistically significant for the 10 µg group but statistically significant for the 25 µg group, there was a decrease observed in the median number of nocturnal voids identified in Table 4 for females over 50 years of age. For example, the 10 µg and 25 µg groups exhibited at least 1.0 fewer nocturnal urinary voids per night on desmopression treatment compared to baseline before treatment. The placebo exhibited only 0.67 fewer nocturnal urinary voids per night compared to baseline.

TABLE 5

Change from baseline to final visit (Day 28) of nocturnal voids (ITT analysis dataset in Part I) for females over 65 years of age.

| Dose | n | mean | stddev | stderr | min | median | max |
|---|---|---|---|---|---|---|---|
| Placebo | 21 | −0.51 | 0.73 | 0.16 | −2.33 | −0.33 | 0.67 |
| 10 ug | 25 | −0.93 | 1.07 | 0.21 | −4.33 | −0.67 | 0.33 |
| 25 ug | 22 | −1.27 | 0.99 | 0.21 | −2.67 | −1.67 | 1.00 |
| 50 ug | 20 | −0.97 | 0.95 | 0.21 | −2.33 | −1.00 | 1.33 |
| 100 ug | 25 | −1.00 | 1.18 | 0.24 | −3.00 | −1.00 | 1.00 |
| Total | 113 | −0.94 | 1.02 | 0.10 | −4.33 | −1.00 | 1.33 | n—population size; stddev—standard deviation; stderr—standard error; min—minimum; and max—maximum Similarly to the other female groups, there was a decrease observed in the median number of nocturnal voids identified in Table 5 for females over 65 years of age at the 25 µg group. For example, the 25 µg group exhibited at least 1.67 fewer nocturnal urinary voids per night on desmopressin treatment compared to baseline before treatment. The placebo exhibited only 0.33 fewer nocturnal urinary voids per night compared to baseline.

Among males, statistically significant differences from placebo were observed for the 100 µg group in the reduction in mean number of nocturnal voids (p=0.0049).

A summary of the changes from baseline to the final visit in the number of nocturnal voids is presented for all males and all males with monitoring (ITT population) in Tables 6 and 7.

TABLE 6

Change from baseline to final visit (Day 28) of nocturnal voids (ITT analysis dataset in Part I) for all males.

| Dose | n | mean | stddev | stderr | min | median | max |
|---|---|---|---|---|---|---|---|
| Placebo | 90 | −0.84 | 1.09 | 0.12 | −4.00 | −1.00 | 1.67 |
| 10 ug | 82 | −0.54 | 0.99 | 0.11 | −3.00 | −0.67 | 2.33 |
| 25 ug | 87 | −0.83 | 1.15 | 0.12 | −3.67 | −0.67 | 2.33 |
| 50 ug | 77 | −1.13 | 1.30 | 0.15 | −5.00 | −1.00 | 1.33 |
| 100 ug | 80 | −1.38 | 1.28 | 0.14 | −4.33 | −1.33 | 4.33 |
| Total | 416 | −0.94 | 1.19 | 0.06 | −5.00 | −1.00 | 4.33 | n—population size;
stddev—standard deviation;
stderr—standard error;
min—minimum; and
max—maximum

TABLE 7

Change from baseline to final visit (Day 28) of nocturnal voids (ITT analysis dataset in Part I) for all males with monitoring.

Figure 2:
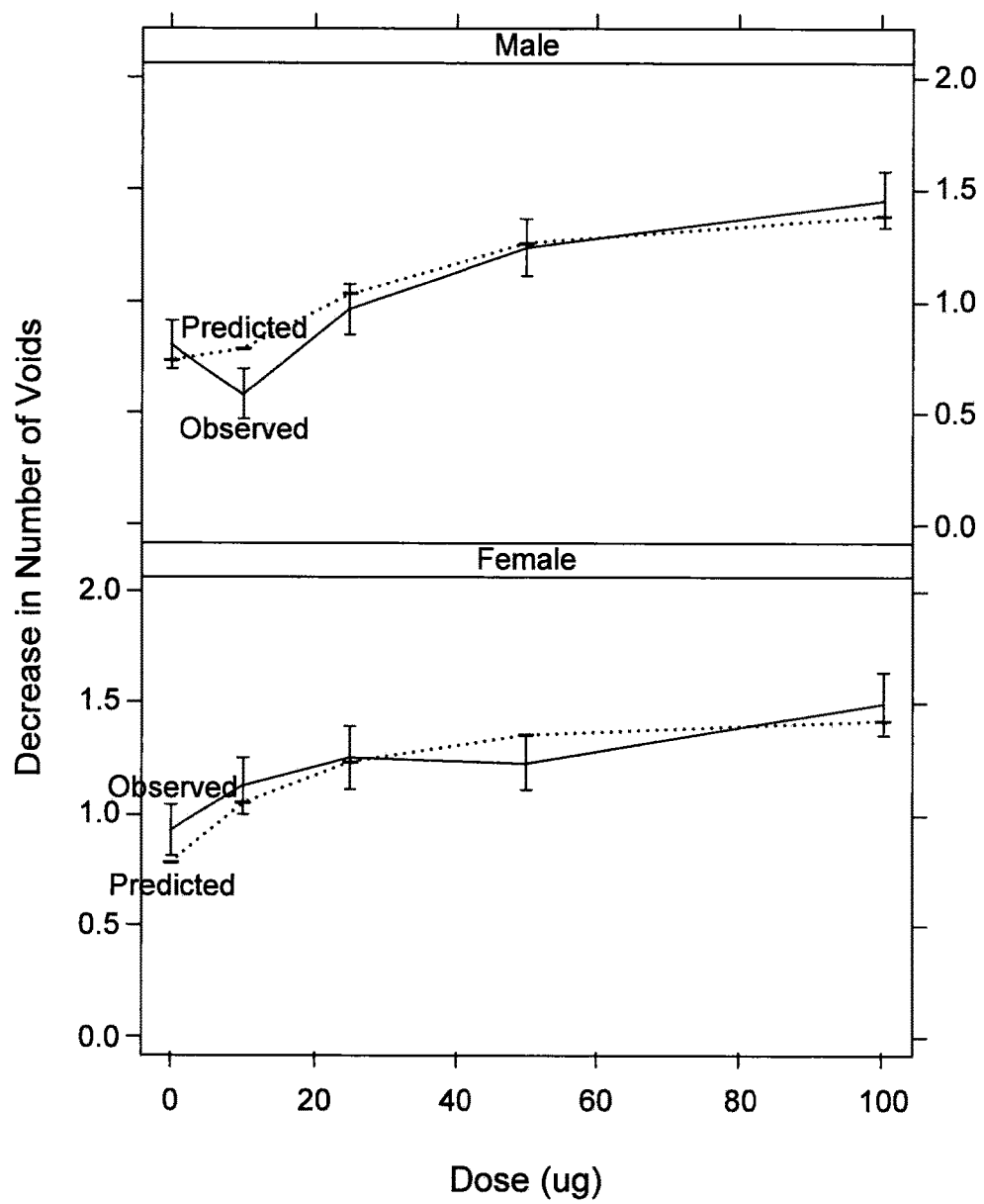
FIG. 2 graphically illustrates the mean observed and predicted change in nocturnal voids by gender and dose.

| Dose | n | mean | stddev | stderr | min | median | max |
|---|---|---|---|---|---|---|---|
| Placebo | 74 | −0.88 | 1.15 | 0.13 | −4.00 | −1.00 | 1.67 |
| 10 ug | 66 | −0.66 | 0.97 | 0.12 | −3.00 | −0.67 | 1.33 |
| 25 ug | 72 | −0.91 | 1.16 | 0.14 | −3.67 | −0.67 | 2.33 |
| 50 ug | 52 | −1.09 | 1.26 | 0.17 | −5.00 | −1.00 | 1.33 |
| 100 ug | 60 | −1.41 | 1.35 | 0.17 | −4.33 | −1.67 | 4.33 |
| Total | 324 | −0.97 | 1.19 | 0.07 | −5.00 | −1.00 | 4.33 | n—population size;
stddev—standard deviation;
stderr—standard error;
min—minimum; and
max—maximum The differences among males and females in the change in number of nocturnal voids is illustrated in FIG. 2. In FIG. 2, the mean observed (full line) and predicted (broken line) change in number of voids by gender and dose demonstrate that the 10 µg and 25 µg groups for females exhibit a larger decrease in nocturnal voids compared to the 10 µg and 25 µg groups for males. The side-by-side comparison in FIG. 2 highlights the gender and dose differences without the requirement of statistical significance.

Based on these gender differences, the minimum effective dose (MED) for females is 25 µg and the MED for males is 100 µg.

Long Term Data—Nocturnal Voids

At one year (Part III), the mean decrease in nocturnal voids per night was 1.4, 1.77, and 2.11 (for 25 µg, 50 µg, and 100 µg, respectively) based on all eligible subjects. The mean decreases in nocturnal voids demonstrate that the decrease observed for the respective concentrations at Day 28 (i.e., Part I) are maintained over a longer treatment period (e.g., 52 weeks) and in some instances, are be even improved. A summary of the changes from baseline is presented for all eligible subjects. With respect to this particular data for Part III, "all eligible subjects" means those subjects that continued through Parts I, II, and III of the study on the same dose (i.e., re-randomized placebo subjects have been excluded) and completed the 1 year diary.

Applicants note that statistical significance cannot be demonstrated for the Part III data on nocturnal voids, as the placebo group was not maintained for Part III. However, based on the data below, the additional decreases in the number of voids can be characterized as clinically significant. As used here, "clinically significant" means a minimum worthwhile effect.

A summary of changes from baseline to day 28 and to week 52 in the number of nocturnal voids is present for all eligible groups in Tables A, B, and C for the 25 µg, 50 µg, and 100 µg doses of desmopressin.

TABLE A

Baseline at day 0 and changes from baseline nocturnal voids for all eligible subjects at the 25 µg dosage.

| | n | Mean | Std Dev | Min | Max |
|---|---|---|---|---|---|
| Day 0 | 86 | 3.24 | 1.27 | 2.00 | 8.67 |
| Day 28 | 86 | −0.98 | 1.15 | −3.33 | 2.33 |
| Week 8 | 67 | −1.16 | 1.13 | −3.33 | 2.67 |
| Week 12 | 57 | −1.29 | 1.14 | −3.00 | 1.33 |
| Week 20 | 42 | −1.48 | 1.05 | −3.67 | 1.67 |
| Week 28 | 67 | −1.44 | 1.20 | −4.33 | 1.00 |
| Week 52 | 86 | −1.41 | 1.26 | −4.67 | 2.33 | n—population size;
stddev—standard deviation;
min—minimum; and
max—maximum

TABLE B

Baseline at day 0 and changes from baseline for all eligible subjects at the 50 µg dosage.

| | n | Mean | Std Dev | Min | Max |
|---|---|---|---|---|---|
| Day 0 | 76 | 3.42 | 1.08 | 2.00 | 7.00 |
| Day 28 | 76 | −1.22 | 1.20 | −5.00 | 2.00 |
| Week 8 | 58 | −1.44 | 1.05 | −4.00 | 1.33 |
| Week 12 | 51 | −1.44 | 1.09 | −3.67 | 1.00 |
| Week 20 | 48 | −1.80 | 1.12 | −4.00 | 1.00 |
| Week 28 | 44 | −1.55 | 1.21 | −5.00 | 1.00 |
| Week 52 | 76 | −1.80 | 1.31 | −6.67 | 0.33 | n—population size;
stddev—standard deviation;
min—minimum; and
max—maximum

TABLE C

Baseline at day 0 and changes from baseline for all eligible subjects at the 100 µg dosage.

| | n | Mean | Std Dev | Min | Max |
|---|---|---|---|---|---|
| Day 0 | 73 | 3.30 | 1.11 | 2.00 | 7.00 |
| Day 28 | 73 | −1.406 | 1.26 | −5.00 | 4.33 |
| Week 8 | 62 | −1.61 | 1.11 | −5.00 | 0.67 |
| Week 12 | 46 | −1.83 | 1.12 | −5.00 | 0.33 |
| Week 20 | 43 | −1.95 | 1.12 | −5.33 | 0 |
| Week 28 | 47 | −1.83 | 0.86 | −4.67 | −0.33 |
| Week 52 | 73 | −2.11 | 1.14 | −6.33 | 0.67 | n—population size;
stddev—standard deviation;
min—minimum; and
max—maximum

Although not statistically significant, the change from baseline to Week 52 in comparison to the change of baseline to day 28 demonstrates that for all eligible subjects, the decrease in frequency of nocturnal voids can be maintained and/or improved over a longer treatment period in a clinically significant manner.

Among females, the reduction in mean number of nocturnal voids from baseline to week 52 maintained or improved, particularly at the 25 µg dose. A summary of changes from baseline to week 52 in the number of nocturnal voids is presented for all females in Tables D-F for the 25 µg, 50 µg, and 100 µg doses of desmopressin.

TABLE D

Baseline at day 0 and changes from baseline for all eligible female subjects at the 25 µg dosage.

|  | n | Mean | Std Dev | Min | Max |
|---|---|---|---|---|---|
| Day 0 | 38 | 3.23 | 1.31 | 2.00 | 8.67 |
| Day 28 | 38 | −1.26 | 1.06 | −3.33 | 0.67 |
| Week 8 | 32 | −1.51 | 0.83 | −3.00 | 0 |
| Week 12 | 29 | −1.66 | 0.98 | −3.00 | 0.67 |
| Week 20 | 22 | −1.68 | 0.96 | −3.00 | 0.67 |
| Week 28 | 27 | −1.86 | 1.18 | −4.33 | 0.33 |
| Week 52 | 38 | −1.75 | 1.16 | −4.67 | 2.00 | n—population size;
stddev—standard deviation;
min—minimum; and
max—maximum

TABLE E

Baseline at day 0 and changes from baseline of nocturnal voids for all eligible female subjects at the 50 µg dosage.

|  | n | Mean | Std Dev | Min | Max |
|---|---|---|---|---|---|
| Day 0 | 31 | 3.17 | 0.70 | 2.00 | 4.67 |
| Day 28 | 31 | −1.30 | 1.16 | −4.00 | 2.00 |
| Week 8 | 26 | −1.60 | 1.045 | −4.00 | 1.00 |
| Week 12 | 23 | −1.62 | 1.072 | −3.33 | 0.67 |
| Week 20 | 18 | −1.93 | 1.11 | −3.67 | 0.33 |
| Week 28 | 19 | −1.89 | 0.88 | −3.33 | 0 |
| Week 52 | 31 | −1.95 | 0.77 | −3.67 | −0.33 | n—population size;
stddev—standard deviation;
min—minimum; and
max—maximum

TABLE F

Baseline at day 0 and changes from baseline of nocturnal voids for all eligible female subjects at the 100 µg dosage.

|  | n | Mean | Std Dev | Min | Max |
|---|---|---|---|---|---|
| Day 0 | 37 | 3.08 | 1.12 | 2.00 | 7.00 |
| Day 28 | 37 | −1.50 | 1.22 | −5.00 | 1.00 |
| Week 8 | 32 | −1.69 | 1.27 | −5.00 | 0.33 |
| Week 12 | 27 | −1.79 | 1.23 | −5.00 | 0.33 |
| Week 20 | 22 | −1.98 | 1.29 | −5.33 | 0 |
| Week 28 | 26 | −1.75 | 1.01 | −4.67 | −0.33 |
| Week 52 | 37 | −2.11 | 1.35 | −6.33 | 0.67 | n—population size;
stddev—standard deviation;
min—minimum; and
max—maximum

Among males, decreases in mean nocturnal voids from baseline to week 52 were observed. A summary of the changes from baseline to week 52 is presented for all eligible male subjects in Tables G-I.

TABLE G

Baseline at day 0 and changes from baseline of nocturnal voids for all eligible male subjects at the 25 µg dosage.

|  | n | Mean | Std Dev | Min | Max |
|---|---|---|---|---|---|
| Day 0 | 48 | 3.26 | 1.24 | 2.00 | 6.33 |
| Day 28 | 48 | −0.76 | 1.18 | −2.67 | 2.33 |
| Week 8 | 35 | −0.84 | 1.27 | −3.33 | 2.67 |
| Week 12 | 28 | −0.90 | 1.19 | −2.67 | 1.33 |
| Week 20 | 20 | −1.25 | 1.13 | −3.67 | 1.67 |

TABLE G-continued

Baseline at day 0 and changes from baseline of nocturnal voids for all eligible male subjects at the 25 µg dosage.

|  | n | Mean | Std Dev | Min | Max |
|---|---|---|---|---|---|
| Week 28 | 40 | −1.15 | 1.13 | −3.67 | 1.00 |
| Week 52 | 48 | −1.13 | 1.28 | −4.33 | 2.33 | n—population size;
stddev—standard deviation;
min—minimum; and
max—maximum

TABLE H

Baseline at day 0 and changes from baseline of nocturnal voids for all eligible male subjects at the 50 µg dosage.

|  | n | Mean | Std Dev | Min | Max |
|---|---|---|---|---|---|
| Day 0 | 45 | 3.59 | 1.25 | 2.00 | 7.00 |
| Day 28 | 45 | −1.16 | 1.23 | −5.00 | 1.00 |
| Week 8 | 32 | −1.31 | 1.04 | −3.67 | 1.33 |
| Week 12 | 28 | −1.30 | 1.11 | −3.67 | 1.00 |
| Week 20 | 30 | −1.73 | 1.13 | −4.00 | 1.00 |
| Week 28 | 25 | −1.28 | 1.37 | −5.00 | 1.00 |
| Week 52 | 45 | −1.69 | 1.58 | −6.67 | 0.33 | n—population size
stddev—standard deviation;
min—minimum; and
max—maximum

TABLE I

Baseline at day 0 and changes from baseline of nocturnal voids for all eligible male subjects at the 100 µg dosage.

|  | n | Mean | Std Dev | Min | Max |
|---|---|---|---|---|---|
| Day 0 | 36 | 3.53 | 1.07 | 2.00 | 6.00 |
| Day 28 | 36 | −1.31 | 1.31 | −3.67 | 4.33 |
| Week 8 | 30 | −1.52 | 0.90 | −3.00 | 0.67 |
| Week 12 | 19 | −1.89 | 0.96 | −3.33 | 0.33 |
| Week 20 | 21 | −1.92 | 0.93 | −3.33 | −0.33 |
| Week 28 | 21 | −1.92 | 0.64 | −3.500 | −1.00 |
| Week 52 | 36 | −2.12 | 0.89 | −4.00 | −0.33 | n—population size
stddev—standard deviation;
min—minimum; and
max—maximum

Tables J-L summarize the data for all subjects with or without an assessment at week 52.

TABLE J

Baseline at day 0 and changes from baseline of nocturnal voids for all subjects at the 25 µg dosage.

|  | n | Mean | Std Dev | Minimum | Maximum |
|---|---|---|---|---|---|
| Day 0 | 158 | 3.38 | 1.35 | 2.00 | 8.67 |
| Day 28 | 158 | −0.96 | 1.12 | −3.67 | 2.33 |
| Week | 100 | −1.31 | 1.16 | −4.67 | 2.67 |
| Week 12 | 85 | −1.42 | 1.23 | −5.00 | 2.00 |
| Week 20 | 60 | −1.61 | 1.16 | −6.00 | 1.67 |
| Week 28 | 87 | −1.39 | 1.14 | −4.33 | 1.33 |
| Week 52 | 86 | −1.41 | 1.26 | −4.67 | 2.33 | n—population size;
stddev—standard deviation;
min—minimum; and
max—maximum

TABLE K

Baseline at day 0 and changes from baseline of nocturnal voids for all subjects at the 50 µg dosage.

|  | n | Mean | Std Dev | Minimum | Maximum |
|---|---|---|---|---|---|
| Day 0 | 157 | 3.39 | 1.05 | 2.00 | 7.33 |
| Day | 157 | −1.10 | 1.19 | −5.00 | 2.00 |
| Week | 92 | −1.43 | 1.28 | −6.33 | 2.33 |
| Week 12 | 77 | −1.51 | 1.16 | −4.00 | 1.33 |
| Week 20 | 64 | −1.71 | 1.16 | −4.00 | 1.00 |
| Week 28 | 61 | −1.55 | 1.28 | −5.00 | 1.67 |
| Week 52 | 76 | −1.80 | 1.31 | −6.67 | 0.33 | n—population size;
stddev—standard deviation;
min—minimum; and
max—maximum

TABLE L

Baseline at day 0 and changes from baseline of nocturnal voids for all subjects at the 100 µg dosage.

|  | n | Mean | Std Dev | Minimum | Maximum |
|---|---|---|---|---|---|
| Day 0 | 160 | 3.22 | 1.06 | 2.00 | 7.33 |
| Day 28 | 160 | −1.31 | 1.23 | −5.00 | 4.33 |
| Week 8 | 104 | −1.47 | 1.08 | −5.00 | 0.67 |
| Week 12 | 81 | −1.73 | 1.04 | −5.00 | 0.33 |
| Week 20 | 64 | −1.86 | 1.08 | −5.33 | 0 |
| Week | 61 | −1.80 | 0.90 | −4.67 | 0.67 |
| Week 52 | 73 | −2.11 | 1.14 | −6.33 | 0.67 | n—population size;
stddev—standard deviation;
min—minimum; and
max—maximum

Secondary Efficacy Endpoints

The secondary efficacy variables were changes from baseline in duration of initial period of undisturbed sleep, duration of total sleep time, and changes in nocturnal urine volume. As noted, the additional secondary efficacy variables data collected (i.e., global (overall) scores of the NQoL, PSQI, and SF-12v2, and scores of the ICIQ-N) are not presented herein.

Duration of Initial Period of Undisturbed Sleep

The most pernicious effect of nocturia is not excessive voiding per se, but its impact on sleep quality and subsequent daytime function as a consequence of sleep disruption. The duration of the initial period of undisturbed sleep increased from baseline to Day 28 in all treatment groups, with greater increases observed with increasing dose of desmopressin. Mean increases in initial sleep duration were 83, 85, and 107 minutes in the 25 µg, 50 µg, and 100 µg groups, respectively. Subjects treated with 25 µg and 50 µg desmopressin had a median increase in their initial period of sleep of approximately 1 hour while subjects treated with the 100 µg dose had a median increase in initial sleep duration of approximately 1½ hours. The 95% confidence intervals for the mean difference from placebo in change from baseline did not include zero for the 25 µg, 50 µg, and 100 µg groups, indicating statistically significant treatment group differences.

A summary of changes from baseline to the final visit in initial period of undisturbed sleep is presented for all groups (ITT population) in Table 8.

TABLE 8

Change from baseline to final visit (Day 28) in duration of initial period of undisturbed sleep (ITT analysis dataset in Part I) for all groups.

| Dose | n | mean | stddev | stderr | min | median | max |
|---|---|---|---|---|---|---|---|
| Placebo | 126 | 39 | 89 | 8 | −273 | 42 | 386 |
| 10 ug | 126 | 51 | 111 | 10 | −317 | 51 | 457 |
| 25 ug | 121 | 83 | 106 | 10 | −104 | 62 | 413 |
| 50 ug | 123 | 85 | 109 | 10 | −233 | 63 | 453 |
| 100 ug | 121 | 107 | 116 | 11 | −166 | 96 | 399 |
| Total | 617 | 72 | 109 | 4 | −317 | 60 | 457 | n—population size;
stddev—standard deviation;
stderr—standard error;
min—minimum; and
max—maximum Although not statistically significant, an increase in the initial period of undisturbed sleep is evident for the 10 µg group as compared to placebo based on median values identified in Table 8 for all groups. For example, the 10 µg group exhibited a median increase of 51 minutes compared to baseline before treatment. The placebo exhibited only a median increase of 42 minutes compared to baseline. Taking into consideration a 5% range from the median increase for the 10 µg group, increases in an initial period of undisturbed sleep range from 48 minutes to 54 minutes compared to baseline before treatment.

A summary of changes from baseline to the final visit in initial period of undisturbed sleep is presented for all females, females over 50 years of age, and females over 65 years of age (ITT population) in Tables 9, 10 and 11.

TABLE 9

Change from baseline to final visit (Day 28) in duration of initial period of undisturbed sleep (ITT analysis dataset in Part I) for all females.

| Dose | n | mean | stddev | stderr | min | median | max |
|---|---|---|---|---|---|---|---|
| Placebo | 49 | 37 | 94 | 13 | −168 | 12 | 386 |
| 10 ug | 60 | 54 | 117 | 15 | −317 | 46 | 457 |
| 25 ug | 51 | 113 | 118 | 17 | −70 | 95 | 413 |
| 50 ug | 61 | 98 | 125 | 16 | −233 | 70 | 453 |
| 100 ug | 57 | 114 | 130 | 17 | −166 | 93 | 399 |
| Total | 278 | 84 | 121 | 7 | −317 | 63 | 457 | n—population size;
stddev—standard deviation;
stderr—standard error;
min—minimum; and
max—maximum Although not statistically significant, an increase in the initial period of undisturbed sleep is evident for the 10 µg and 25 µg groups as compared to placebo based on median values identified in Table 9 for all female patients. For example, the 10 µg group exhibited a median increase of 46 minutes and the 25 µg group exhibited a median increase of 95 minutes compared to baseline before treatment. The placebo exhibited only a median increase of 12 minutes compared to baseline. Taking into consideration a 20% range from the median increase for the 10 µg and 25 µg groups, increases in an initial period of undisturbed sleep ranges from 37 minutes to 114 minutes, such as from 37 minutes to 55 minutes for the 10 µg group and from 76 minutes to 114 minutes for the 25 µg group compared to baseline for all females.

TABLE 10

Change from baseline to final visit (Day 28) in duration of initial period of undisturbed sleep (ITT analysis dataset in Part I) for females over 50 years of age.

| Dose | n | mean | stddev | stderr | min | median | max |
|---|---|---|---|---|---|---|---|
| Placebo | 38 | 25 | 77 | 13 | −168 | 11 | 168 |
| 10 ug | 40 | 33 | 112 | 18 | −317 | 27 | 293 |
| 25 ug | 39 | 122 | 123 | 20 | −70 | 96 | 413 |
| 50 ug | 48 | 83 | 126 | 18 | −233 | 63 | 453 |
| 100 ug | 42 | 108 | 129 | 20 | −166 | 89 | 330 |
| Total | 207 | 75 | 121 | 8 | −317 | 54 | 453 | n—population size;
stddev—standard deviation;
stderr—standard error;
min—minimum; and
max—maximum Although not statistically significant, an increase in the initial period of undisturbed sleep is evident for the 10 μg and 25 μg groups as compared to placebo based on median values identified in Table 10 for female patients over 50 years of age. For example, the 10 μg group exhibited a median increase of 27 minutes and the 25 μg group exhibited a median increase of 96 minutes compared to baseline before treatment. The placebo exhibited only a median increase of 11 minutes compared to baseline. Taking into consideration a 20% range from the median increase for the 10 μg and 25 μg groups, increases in an initial period of undisturbed sleep ranges from 22 minutes to 115 minutes, such as from 22 minutes to 32 minutes for the 10 μg group and from 77 minutes to 115 minutes for the 25 μg group, compared to baseline before treatment for females over 50 years of age.

TABLE 11

Change from baseline to final visit (Day 28) in duration of initial period of undisturbed sleep (ITT analysis dataset in Part I) for females over 65 years of age.

| Dose | n | mean | stddev | stderr | min | median | max |
|---|---|---|---|---|---|---|---|
| Placebo | 19 | 50 | 60 | 14 | −50 | 52 | 168 |
| 10 ug | 18 | 18 | 125 | 29 | −317 | 46 | 243 |
| 25 ug | 15 | 131 | 126 | 32 | −70 | 113 | 413 |
| 50 ug | 19 | 42 | 131 | 30 | −233 | 30 | 288 |
| 100 ug | 21 | 81 | 119 | 26 | −118 | 70 | 275 |
| Total | 92 | 62 | 118 | 12 | −317 | 53 | 413 | n—population size;
stddev—standard deviation;
stderr—standard error;
min—minimum; and
max—maximum Although not statistically significant, an increase in the initial period of undisturbed sleep is evident for the 25 μg group as compared to placebo based on median values identified in Table 11 for female patients over 65 years of age. For example, the 25 μg group exhibited a median increase of 113 minutes compared to baseline before treatment. The placebo exhibited only a median increase of 52 minutes compared to baseline. Taking into consideration a 20% range from the median increase for the 25 μg group, increases in an initial period of undisturbed sleep range from 90 minutes to 136 minutes, such as from 102 minutes to 124 minutes, compared to baseline before treatment for females over 65 years of age.

A summary of changes from baseline to the final visit in initial period of undisturbed sleep is presented for all males and all males with monitoring (ITT population) in Tables 12 and 13.

TABLE 12

Change from baseline to final visit (Day 28) in duration of initial period of undisturbed sleep (ITT analysis dataset in Part I) for all males.

| Dose | n | mean | stddev | stderr | min | median | max |
|---|---|---|---|---|---|---|---|
| Placebo | 77 | 40 | 86 | 10 | −273 | 47 | 285 |
| 10 ug | 66 | 48 | 107 | 13 | −158 | 56 | 370 |
| 25 ug | 70 | 61 | 90 | 11 | −104 | 55 | 259 |
| 50 ug | 62 | 72 | 90 | 11 | −165 | 55 | 292 |
| 100 ug | 64 | 100 | 103 | 13 | −152 | 101 | 363 |
| Total | 339 | 63 | 97 | 5 | −273 | 58 | 370 | n—population size;
stddev—standard deviation;
stderr—standard error;
min—minimum; and
max—maximum

TABLE 13

Change from baseline to final visit (Day 28) in duration of initial period of undisturbed sleep (ITT analysis dataset in Part I) for all males with monitoring.

| Dose | n | mean | stddev | stderr | min | median | max |
|---|---|---|---|---|---|---|---|
| Placebo | 70 | 44 | 85 | 10 | −273 | 48 | 285 |
| 10 ug | 60 | 54 | 107 | 14 | −145 | 59 | 370 |
| 25 ug | 62 | 57 | 87 | 11 | −104 | 54 | 259 |
| 50 ug | 45 | 64 | 89 | 13 | −165 | 59 | 291 |
| 100 ug | 52 | 108 | 103 | 14 | −152 | 116 | 363 |
| Total | 289 | 64 | 96 | 6 | −273 | 58 | 370 | n—population size;
stddev—standard deviation;
stderr—standard error;
min—minimum; and
max—maximum Duration of Total Sleep Time Total sleep time increased in all treatment groups in Part I; however, no pattern was observed by dose of desmopressin. Based on F-tests of effects, computed overall sleep duration and reported overall sleep duration were statistically significant predictors of change from baseline to Day 28 in total sleep time ($p < 0.0001$).

A summary of change from baseline to Day 28 in total sleep time is presented by treatment group in Table 14.

TABLE 14

Change from baseline to final visit (Day 28) in total sleep time (Part I).

| | Total Sleep Time (min) | | | | |
|---|---|---|---|---|---|
| | Placebo (N = 156) | 10 μg (N = 155) | 25 μg (N = 152) | 50 μg (N = 148) | 100 μg (N = 146) |
| Calculated Sleep Time | (N = 156) | (N = 155) | (N = 152) | (N = 148) | (N = 146) |

TABLE 14-continued

Change from baseline to final visit (Day 28) in total sleep time (Part I).

| | Total Sleep Time (min) | | | | |
|---|---|---|---|---|---|
| | Placebo (N = 156) | 10 µg (N = 155) | 25 µg (N = 152) | 50 µg (N = 148) | 100 µg (N = 146) |
| Baseline | | | | | |
| Mean (SD) | 399 (97.0) | 397 (92.2) | 397 (90.3) | 404 (95.8) | 414 (85.0) |
| Median | 410 | 402 | 412 | 415 | 418 |
| Minimum, maximum | (15, 732) | (135, 720) | (95, 577) | (20, 577) | (72, 638) |
| Change from Baseline | (N = 138) | (N = 137) | (N = 142) | (N = 138) | (N = 133) |
| Mean (SD) | 31.4 (89.22) | 9.7 (91.40) | 19.7 (71.67) | 24.2 (79.60) | 9.7 (77.33) |
| Median | 19.5 | 10.0 | 15.3 | 14.2 | 12.0 |
| Minimum, maximum | (−167, 420) | (−332, 282) | (−191, 318) | (−235, 218) | (−300, 227) |
| Reported Sleep Time Baseline | (N = 156) | (N = 155) | (N = 152) | (N = 148) | (N = 146) |
| Mean (SD) | 403 (83.7) | 411 (72.8) | 401 (77.8) | 403 (83.7) | 413 (81.3) |
| Median | 408 | 400 | 410 | 409 | 410 |
| Minimum, maximum | (135, 625) | (190, 613) | (77, 555) | (100, 580) | (100, 674) |
| Change from Baseline | (N = 139) | (N = 137) | (N = 141) | (N = 138) | (N = 133) |
| Mean (SD) | 24.6 (80.66) | 7.8 (58.55) | 15.9 (53.92) | 24.9 (72.21) | 19.0 (68.94) |
| Median | 20.3 | 10.0 | 10.0 | 20.0 | 20.0 |
| Minimum, maximum | (−135, 525) | (−130, 163) | (−113, 228) | (−168, 293) | (−160, 197) |

Change in Urine Volume

Pharmacodynamic studies indicate that desmopressin has a very pronounced antidiuretic effect. Nocturnal urine volume decreased in all treatment groups, with greater decreases observed with increasing desmopressin dose. For change from baseline to Day 28 in nocturnal urine volume, based on F-tests of effects, treatment (p<0.0001), age (p=0.0067), and baseline nocturnal urine volume (p<0.0001) were statistically significant predictors for change from baseline. The 95% confidence intervals for the mean difference from placebo in change from baseline did not include zero for the 25 µg, 50 µg, and 100 µg groups, indicating statistically significant treatment group differences.

Similarly, total urine volume, which included both day and nocturnal voids, decreased in all treatment groups, with greater decreases observed with increasing desmopressin dose. In the 50 µg group, a slight mean increase in urine output occurred during the day and, as a result, the nocturnal mean urine reduction was greater than the total mean urine reduction.

Figure 3:
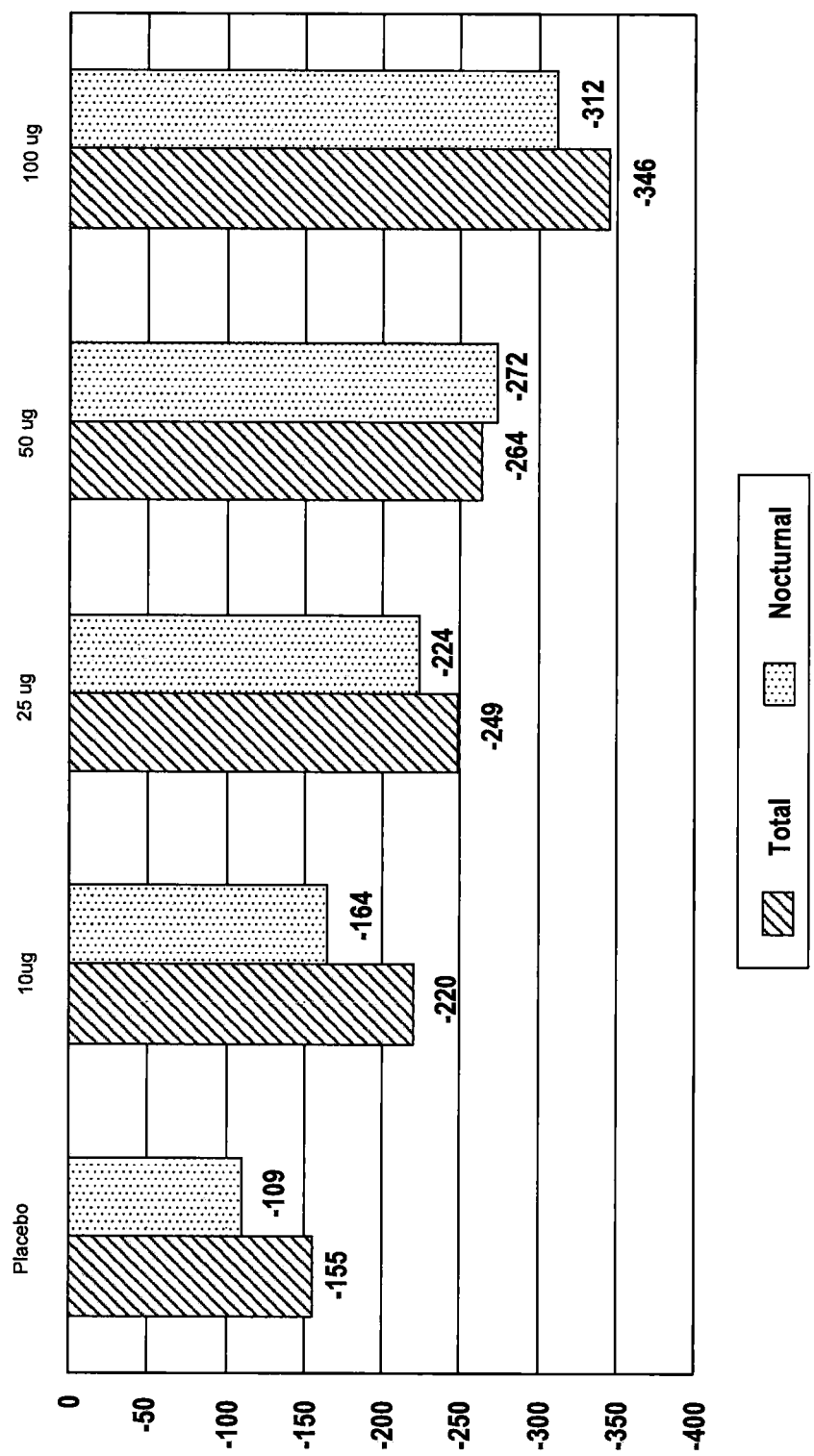
FIG. 3 graphically illustrates the decrease in total and nocturnal urine volume for the placebo, 10 µg, 25 µg, 50 µg, and 100 µg groups.

As shown in FIG. 3, the majority of the decrease in total urine volume was a decrease in nocturnal volume. The decreases in nocturnal urine volume for the 25 µg, 50 µg, and 100 µg groups were statistically significant.

A summary of changes from baseline to the final visit in of nocturnal urine volume is presented for all groups (ITT population) in Table 15.

TABLE 15

Change from baseline to final visit (Day 28) of nocturnal urine volume (ITT analysis dataset in Part I) for all groups.

| Dose | n | mean | stddev | stderr | min | median | max |
|---|---|---|---|---|---|---|---|
| Placebo | 140 | −109 | 246 | 21 | −817 | −94 | 800 |
| 10 ug | 137 | −164 | 277 | 24 | −983 | −150 | 568 |

TABLE 15-continued

Change from baseline to final visit (Day 28) of nocturnal urine volume (ITT analysis dataset in Part I) for all groups.

| Dose | n | mean | stddev | stderr | min | median | max |
|---|---|---|---|---|---|---|---|
| 25 ug | 144 | −224 | 264 | 22 | −1,084 | −233 | 567 |
| 50 ug | 138 | −272 | 296 | 25 | −1,017 | −233 | 717 |
| 100 ug | 135 | −312 | 275 | 24 | −1,238 | −283 | 408 |
| Total | 694 | −216 | 281 | 11 | −1,238 | −200 | 800 | n—population size;
stddev—standard deviation;
stderr—standard error;
min—minimum; and
max—maximum Although not statistically significant, a decrease in nocturnal urine volume is evident for the 10 µg group as compared to placebo based on median decreases identified in Table 15 for all groups. For example, the 10 µg group exhibited a median value decrease of 150 ml compared to baseline before treatment. The placebo exhibited only a median decrease of 94 ml compared to baseline. Taking into consideration a 20% range from the median decrease for the 10 µg group, decreases in nocturnal urine volume include at least 120 ml and for example, range from 120 ml to 180 ml, compared to baseline before treatment for all groups.

A summary of changes from baseline to the final visit of nocturnal urine volume is presented for all females, females over 50 years of age, and females over 65 years of age (ITT population) in Tables 16, 17 and 18.

TABLE 16

Change from baseline to final visit (Day 28) of nocturnal urine volume (ITT analysis dataset in Part I) for all females.

| Dose | n | mean | stddev | stderr | min | median | max |
|---|---|---|---|---|---|---|---|
| Placebo | 60 | −86 | 278 | 36 | −817 | −56 | 800 |
| 10 ug | 66 | −207 | 292 | 36 | −983 | −179 | 538 |
| 25 ug | 61 | −307 | 276 | 35 | −1,084 | −298 | 292 |
| 50 ug | 66 | −257 | 282 | 35 | −1,017 | −204 | 717 |
| 100 ug | 60 | −321 | 239 | 31 | −933 | −283 | 25 |
| Total | 313 | −236 | 285 | 16 | −1,084 | −217 | 800 | n—population size;
stddev—standard deviation;
stderr—standard error;
min—minimum; and
max—maximum Although not statistically significant, a decrease in nocturnal urine volume is evident for the 10 μg and 25 μg groups as compared to placebo based on median decreases identified in Table 16 for all females. For example, the 10 μg group exhibited a median decrease of 179 ml and the 25 μg group exhibited a median decrease of 298 ml compared to baseline before treatment. The placebo exhibited only a median decrease of 56 ml compared to baseline. Taking into consideration a 20% range from the median decreases for the 10 μg and 25 μg groups, decreases in nocturnal urine volume include at least 143 ml and for example, range from 143 ml to 358 ml, such as from 143 ml to 215 ml for the 10 μg group and from 238 ml to 358 ml for the 25 μg group, compared to baseline before treatment for all females.

TABLE 17

Change from baseline to final visit (Day 28) of nocturnal urine volume (ITT analysis dataset in Part I) for females over 50 years of age.

| Dose | n | mean | stddev | stderr | min | median | max |
|---|---|---|---|---|---|---|---|
| Placebo | 44 | −102 | 242 | 36 | −817 | −56 | 268 |
| 10 ug | 45 | −197 | 319 | 48 | −983 | −150 | 538 |
| 25 ug | 46 | −356 | 281 | 41 | −1,084 | −383 | 292 |
| 50 ug | 52 | −249 | 289 | 40 | −1,017 | −196 | 717 |
| 100 ug | 45 | −317 | 252 | 38 | −933 | −275 | 25 |
| Total | 232 | −245 | 290 | 19 | −1,084 | −217 | 717 | n—population size;
stddev—standard deviation;
stderr—standard error;
min—minimum; and
max—maximum Although not statistically significant, a decrease in nocturnal urine volume is evident for the 10 μg and 25 μg groups as compared to placebo based on median decreases identified in Table 17 for females over 50 years of age. For example, the 10 μg group exhibited a median decrease of 150 ml and the 25 μg group exhibited a median decrease of 383 ml compared to baseline before treatment. The placebo exhibited a median decrease of 56 ml compared to baseline. Taking into consideration a 20% range from the median decreases for the 10 μg and 25 μg groups, decreases in nocturnal urine volume include at least 120 ml and for example, range from 120 ml to 460 ml, such as from 120 ml to 180 ml for the 10 μg group and from 306 ml to 460 ml for the 25 μg group, compared to baseline before treatment for females over 50 years of age.

TABLE 18

Change from baseline to final visit (Day 28) of nocturnal urine volume (ITT analysis dataset in Part I) for females over 65 years of age.

| Dose | n | mean | stddev | stderr | min | median | max |
|---|---|---|---|---|---|---|---|
| Placebo | 20 | −90 | 170 | 38 | −557 | −47 | 133 |
| 10 ug | 22 | −91 | 302 | 64 | −742 | −54 | 538 |
| 25 ug | 19 | −372 | 270 | 62 | −867 | −383 | 25 |
| 50 ug | 20 | −208 | 323 | 72 | −703 | −203 | 717 |
| 100 ug | 23 | −323 | 261 | 54 | −817 | −285 | 25 |
| Total | 104 | −216 | 290 | 28 | −867 | −171 | 717 | n—population size;
stddev—standard deviation;
stderr—standard error;
min—minimum; and
max—maximum Although not statistically significant, a decrease in nocturnal urine volume is evident for the 25 μg group as compared to placebo based on median decreases identified in Table 18 for females over 65 years of age. For example, the 25 μg group exhibited a median decrease of 383 ml compared to the placebo median decrease of 47 ml compared to baseline before treatment. Taking into consideration a 20% range from the median decrease for the 25 μg group, decreases in nocturnal urine volume include at least 211 ml and for example, range from 238 ml to 290 ml, compared to baseline before treatment for females over 65 years of age.

A summary of changes from baseline to the final visit of nocturnal urine volume is presented for all males and all males with monitoring (ITT population) in Tables 19 and 20.

TABLE 19

Change from baseline to final visit (Day 28) of nocturnal urine volume (ITT analysis dataset in Part I) for all males.

| Dose | n | mean | stddev | stderr | min | median | max |
|---|---|---|---|---|---|---|---|
| Placebo | 80 | −125 | 219 | 25 | −727 | −111 | 583 |
| 10 ug | 71 | −125 | 257 | 30 | −750 | −117 | 568 |
| 25 ug | 83 | −162 | 238 | 26 | −873 | −200 | 567 |
| 50 ug | 72 | −286 | 309 | 36 | −984 | −246 | 422 |
| 100 ug | 75 | −306 | 302 | 35 | −1,238 | −270 | 408 |
| Total | 381 | −199 | 276 | 14 | −1,238 | −192 | 583 | n—population size;
stddev—standard deviation;
stderr—standard error;
min—minimum; and
max—maximum

TABLE 20

Change from baseline to final visit (Day 28) of nocturnal urine volume (ITT analysis dataset in Part I) for all males with monitoring.

| Dose | n | mean | stddev | stderr | min | median | max |
|---|---|---|---|---|---|---|---|
| Placebo | 72 | −128 | 229 | 27 | −727 | −111 | 583 |
| 10 ug | 63 | −122 | 269 | 34 | −750 | −83 | 568 |
| 25 ug | 72 | −146 | 219 | 26 | −608 | −167 | 567 |
| 50 ug | 50 | −286 | 313 | 44 | −984 | −235 | 357 |
| 100 ug | 60 | −296 | 275 | 36 | −867 | −264 | 408 |
| Total | 317 | −188 | 268 | 15 | −984 | −183 | 583 | n—population size;
stddev—standard deviation;
stderr—standard error;
min—minimum; and
max—maximum From Table 20, a decrease in nocturnal urine volume is evident for the 100 µg group as compared to placebo based on median decreases from baseline. For example, the 100 µg group exhibited a median decrease of 264 ml compared to baseline before treatment. The placebo exhibited only a median decrease of 111 ml compared to baseline. Taking into consideration a 20% range from the median decrease for the 100 µg group, decreases in nocturnal urine volume include at least 211 ml and for example, range from 211 ml to 317 ml, such as from 238 ml to 290 ml, compared to baseline before treatment for males with monitoring.

Figure 4:
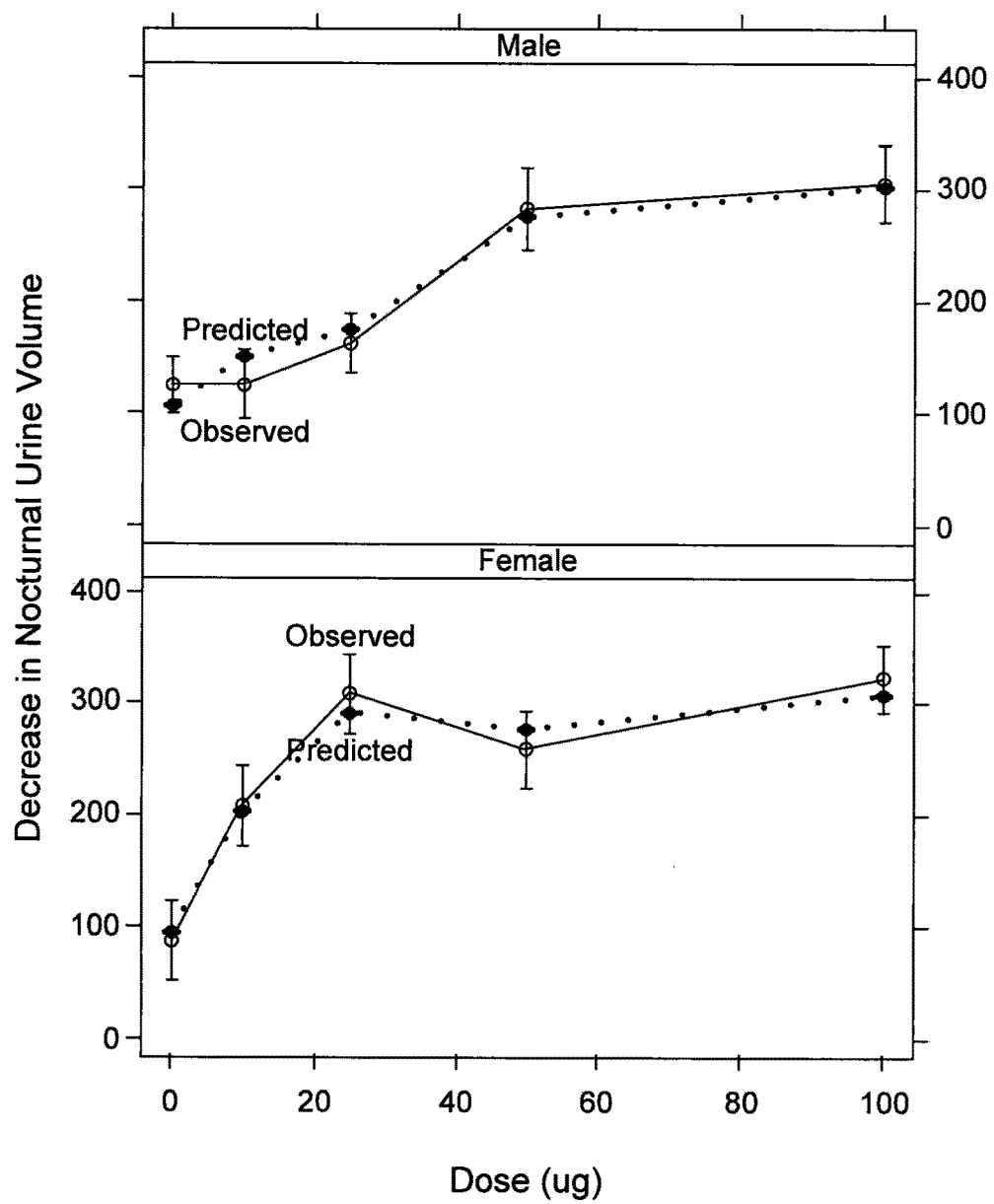
FIG. 4 graphically illustrates the mean observed and predicted change in nocturnal urine by gender and dose.

The differences among males and females in the change in nocturnal urine volume is illustrated in FIG. 4. In FIG. 4, the mean observed (full line) and predicted (broken line) change in nocturnal urine volume demonstrate the greater sensitivity to lower doses (i.e., 10 µg and 25 µg groups) in females than males. The side-by-side comparison in FIG. 4 highlights the gender and dose differences without the requirement of statistical significance.

Statistical/Analytical Issues—Handling of Dropouts or Missing Data

Missing values concerning number of nocturnal voids at Day 8, Day 15, Day 22, and Day 28 in Part I were imputed using last observation carried forward (LOCF). Missing values concerning sleep disturbance and urine volume (for average 24-hour urine volume and average nocturnal urine volume) were not imputed.

Drug Dose, Drug Concentration and Relationships to Response

Four doses of desmopressin (10 µg, 25 µg, 50 µg, and 100 µg) were included in this study. Both the primary endpoint of the number of nocturnal voids generally demonstrated an increase in efficacy with increasing dose of desmopressin. An additional analysis of the primary efficacy endpoint was performed by gender and demonstrated gender differences in response. Among females, efficacy was demonstrated for the 25 µg, 50 µg, and 100 µg doses of desmopressin for the primary endpoint. Among males, the 100 µg desmopressin dose was superior to placebo for the primary endpoint. Based on these gender differences, the MED for females is 25 µg and for males is 100 µg.

Efficacy Conclusions

Four doses of desmopressin (10 µg, 25 µg, 50 µg, and 100 µg) were compared to placebo in this study for the primary endpoint in Part I: change in the mean number of nocturnal voids from baseline to final visit (Day 28).

The mean number of nocturnal voids decreased from baseline to Day 28 in all treatment groups, with greater decreases observed with increasing dose of desmopressin. The reduction in mean number of nocturnal voids, compared to placebo, was statistically significant for the 100 µg and 50 µg groups. The trend of greater decreases in mean number of nocturnal voids with increasing dose of desmopressin was evident in subjects stratified by age (<65 years, ≥65 years) and in subjects with nocturnal polyuria. Too few subjects did not have nocturnal polyuria to make meaningful comparisons. The reduction in mean number of nocturnal voids, compared to placebo, was statistically significant for the 100 µg group for all 4 stratification factors and for the 50 µg group for subjects with nocturnal polyuria. When decreases in mean number of nocturnal voids were examined by week of treatment, statistically significant differences, compared to placebo, were observed for the 25 µg, 50 µg, and 100 µg doses on Day 8 and Day 15 of treatment, with significant differences for the 2 higher doses also on Day 22 and Day 28.

An additional analysis of the primary efficacy endpoint was performed by gender, and a gender difference in response was observed. Among females, the reduction in mean number of nocturnal voids was statistically significantly superior to placebo for the 100 µg, 50 µg, and 25 µg groups. Among males, statistically significant differences from placebo were observed for the primary endpoint for the 100 µg group. Based on these gender differences, the MED for females is 25 µg and the MED for males is 100 µg.

Nocturnal urine volume, as well as total urine volume, decreased in all treatment groups, with greater decreases observed with increasing desmopressin dose. Based on 95% confidence intervals that did not include zero, the decreases in nocturnal urine volume for the 25 µg, 50 µg, and 100 µg groups were statistically significant.

The secondary efficacy endpoint of change from baseline to final visit (Day 28) in duration of initial period of undisturbed sleep also demonstrated greater increases with increasing dose of desmopressin. Subjects treated with 25 µg and 50 µg had a median increase in their initial period of sleep of approximately 1 hour while subjects treated with the 100 µg dose had a median increase in initial sleep duration of approximately 1½ hours; the 95% confidence intervals for the mean difference from placebo indicated statistically significant differences for the 25 µg, 50 µg, and 100 µg groups.

In summary, the efficacy of 100 µg desmopressin was demonstrated superior to placebo for the primary endpoint overall; for the primary endpoint, among males and among females; proportions of subjects with >50% and >75% reductions in the mean number of nocturnal voids; change from baseline to final visit (Day 28) in duration of the initial period of undisturbed sleep; and reductions in nocturnal urine volume. The efficacy of 50 µg desmopressin was superior to placebo for change from baseline to Day 28 in the mean number of nocturnal voids; for the primary endpoint among females; duration of the initial period of undisturbed sleep; and reductions in nocturnal urine volume. In addition, numerical superiority was observed for 50 µg desmopressin compared to placebo for the proportion of subjects with >33% reductions (53% vs. 47%), >50% reductions (28% vs. 20%), and >75% reductions (10% vs. 5%) in the mean number of nocturnal voids on Day 28. The 25 µg dose was superior to placebo for the primary endpoint among females; in reducing the mean number of nocturnal voids; change from baseline to Day 28 in duration of the initial period of undisturbed sleep; and reductions in nocturnal urine volume. The 10 µg dose did not demonstrate statistically superiority over placebo for the primary or secondary efficacy endpoint. A gender difference in response was observed. For the primary endpoint, superiority to placebo was demonstrated for the 25 µg, 50 µg, and 100 µg doses among females and for the 100 µg dose among males.

Results of Study CS29 demonstrated that the 100 µg dose was clearly efficacious, while the 10 µg dose can be considered subtherapeutic for the primary efficacy parameter for the overall study population. Based on the observed gender differences, the MED for females is 25 µg and the MED for males is 100 µg.

At 1 year, the mean decrease in nocturnal voids was 1.4, 1.77, and 2.11 (for 25 µg, 50 µg, and 100 µg, respectively) based on all eligible subjects.

Adverse Events Leading to Discontinuation: Hyponatraemia and Serum Sodium Monitoring The reported event of hyponatraemia, defined as serum sodium <130 mmol/L, was an adverse event of special interest. A total of 34 (4%) subjects developed hyponatraemia during Part I. There was essentially no difference in the occurrence of hyponatraemia between placebo and the 10 μg and 25 μg groups; however, the incidence of serum sodium <130 mmol/L rose from 1.3% in the 25 μg group to 7.0% in the 50 μg group and to 11.3% in the 100 μg group. Hyponatraemia tended to occur early in treatment, usually during the first week, and was more common in subjects 65 years of age.

Since hyponatraemia is a potentially serious adverse event associated with daily doses of desmopressin, serum sodium was monitored throughout the study in all subjects. Based on the results of Study CS29, the following sodium monitoring criteria were applied to the CS29 data.

In subjects below 50 years of age:
Baseline serum sodium level ≥135 mmol/L.
In subjects 50 years of age and above:
Baseline serum sodium level ≥135 mmol/L
Day 4 serum sodium level ≥135 mmol/L
Day 28 serum sodium level ≥135 mmol/L.

Subjects who did not meet these criteria would be removed. Without monitoring, serum sodium levels below 125 mmol/L occurred in 3 subjects each in the 50 μg and 100 μg groups on Day 4 and 1 subject in each of these groups on Day 8. It should be remembered that serum sodium monitoring occurred the day after the evening dose of study drug.

Based on these findings, serum sodium monitoring at Day 4 and Day 28 is recommended in males older than 65 years of age at 100 μg. The serum sodium levels at Day 4 and Day 28 should be ≥135 mmol/L. In males below 65 years of age who are treated at 100 μg, no further monitoring appears to be warranted. In female subjects who are treated at 25 μg, no further monitoring appears to be warranted.

Dosing

Results of Study CS29 demonstrated that the 10 μg dose was considered a subtherapeutic dose for the primary efficacy parameters when looking at the overall population. While the 100 μg dose was clearly efficacious, the risk of hyponatraemia was greater than with the lower doses of desmopressin. Although not as effective as the 100 μg dose, the benefit:risk ratio favored the 25 μg and 50 μg doses. The 25 μg dose was clearly less likely to cause hyponatraemia than the 50 μg and 100 μg doses and was statistically significantly superior to placebo in the primary efficacy endpoint among females. Among males, the 100 μg desmopressin dose was statistically significantly superior to placebo for the primary endpoint. Based on these gender differences, the MED for females is 25 μg and the MED for males is 100 μg.

REFERENCES 1. van Kerrebroeck P et al. The Standardization of Terminology in Nocturia: Report from the Standardisation Sub-committee of the International Continence Society. Neurourol Urodynam 2002; 21:179-183
2. Weiss J P, Blaivas J G. Nocturia. J Urol 2000; 163: 5-12
3. Robertson G L. Nocturnal Polyuria. BJU Int 1999; 84 (suppl 1):17-19
4. Kirkland J L et al. Patterns of urine flow and electrolyte excretion in healthy elderly people. BMJ 1983; 287: 1665-1667
5. van Kerrebroeck P et al. The Standardization of Terminology in Nocturia: Report from the Standardisation Sub-committee of the International Continence Society. Neurourol Urodynam 2002; 21:179-183
6. Asplund R., Aberg H. Diurnal variation in the levels of antidiuretic hormone in the elderly. J Int Med 1991; 229: 131-134
7. Matthiesen T B et al. Nocturnal polyuria and natriuresis in male patients with nocturia and lower urinary tract symptoms. J Urol 1996; 156:1292-1299
8. Bodo G et al. Circadian antidiuretic hormone variation in elderly men complaining of persistent nocturia after urinary flow obstruction removal. Scan J Urol Nephrol 1998; 32: 320-24
9. Kikuchi Y. Participation of atrial natriuretic peptide levels and arginine vasopressin in aged persons with nocturia. Jpn J Urol 1995; 86:1651-1659
10. Moon D G et al. Antidiuretic hormone in elderly male patients with severe nocturia: a circadian study. BJU Int 2004; 94: 571-575
11. Graugaard-Jensen C et al. Nocturia and circadian blood pressure profile in healthy elderly male volunteers. J Urol 2006; 176: 1034-1039
12. Natsume O. A clinical investigation of nocturnal polyuria in patients with nocturia: A diurnal variation in arginine vasopressin secretion and its relevance to mean blood pressure. J Urol 2006; 176: 660-664
13. George C P L et al. Diurnal variation of plasma vasopressin in man. J Clin Endocrin Met 1975; 41: 332-338
14. Johnson T M et al. Arginine vasopressin and nocturnal polyuria in older adults with frequent nighttime voiding. J Urol 2003; 170: 480-484
15. Beck L H, Burkart J M. Aging changes in renal function. In: Hazzard W R et al., editors. Principles of geriatric medicine and gerontology. McGraw-Hill Book Co., 1990: 555-564
16. van Dijk L et al. Nocturia in the Dutch adult population. BJU Int 2002; 90:644-648
17. Hakkinen J T et al. Incidence of nocturia in 50 to 80-year-old Finnish Men. J Urol 2006; 176:2541-2545
18. Tikkinin K A O et al. Is nocturia equally common among men and women? A population based study in Finland. J Urol 2006; 175:596-600
19. Diokno A C et al. Prevalence of urinary incontinence and other urological symptoms in the noninstitutionalized elderly. J Urol 1986; 136:1022-1025
20. Sommer P et al. Voiding patterns in men evaluated using a questionnaire survey. Br J Urol 1990; 65:155-160
21. Fultz N H, Herzog A R. Epidemiology of urinary symptoms in the geriatric population. Urol Clin North Am 1996; 23:1-10
22. Chute C G et al. The prevalence of prostatism: A population-based survey of urinary symptoms. J Urol 1993; 150:85-89
23. Sommer P et al. Voiding patterns and prevalence of incontinence in women: A questionnaire survey. Br J Urol 1990; 66:12-15
24. Britton J P et al. Prevalence of urinary symptoms in men over age 60 Br J Urol 1990; 66:175-176
25. Samuelsson E et al. A population study of urinary incontinence and nocturia among women aged 20-59 years: Prevalence, well-being and wish for treatment Acta Obstet Gynecol Scan 1997; 76: 74-80
26. Blanker M H et al. Normal voiding patterns and determinants of increased diurnal and nocturnal voiding frequency in elderly men J Urol 2000; 164:1201-1205
27. Swithinbank L V, Abrams P. A detailed description, by age, of lower urinary tractsymptoms in a group of community dwelling women. BJU Int 2000; 85 (suppl 2): 19-24

28. Malmsten U G H et al. Urinary incontinence and lower urinary tract symptoms: An epidemiological study of men aged 45 to 99 years. J Urol 1997; 158: 1733-1737
29. Irwin D E et al. Population-based survey of urinary incontinence, overactive bladder and other lower urinary tract symptoms in five countries: Results of the EPIC study. Eur Urol 2006, doi:10.1016/j.eururo.2006.09.019
30. Jolleys J V et al. Urinary symptoms in the community: How bothersome are they?Br J Urol 1994; 74: 551-555
31. Coyne K S et al. The prevalence of nocturia and its effect on health-related quality of life and sleep in a community sample in the USA. BJU Int 2003; 92: 948-954
32. Middelkoop H A M et al. Subjective sleep characteristics of 1485 males and females aged 50-93: Effects of sex and age, and factors related to self-evaluated quality of sleep. J Gerontol A Biol Sci Med Sci 1996; 51:M108-M115
33. Asplund R et al. Nocturnal micturition, sleep and well-being in women ages 40-64 years. Maturitas 1996; 24: 73-81
34. Hetta J et al. Mood alterations and sleep. Ann Clin Res 1985; 17: 252-256
35. Manabe K et al. Sleep patterns and mortality among elderly patients in a geriatric hospital. Gerontology 2002; 46: 318-322
36. Akerstedt T et al. A prospective study of fatal occupational accidents—relationship to sleeping difficulties and occupational factors. J Sleep Res 2002; 11: 69-71
37. Kobelt G et al. Productivity, vitality and utility in a group of professionally active individuals with nocturia. BJU Int 2003; 91: 190-195
38. Stewart R B et al. Nocturia: A risk factor for falls in the elderly J Am Geriatr Soc 1992; 40:1217-1220
39. Baker S P, Harvey A H. Fall injuries in the elderly. Clin Geriatr Med 1985; 1:501-508
40. Stewart R B et al. Nocturia: A risk factor for falls in the elderly J Am Geriatr Soc 1992; 40:1217-1220
41. Vilhardt H. Basic pharmacology of desmopressin: a review. Drug Invest 1990; 2 (suppl 5): 2-8

Those skilled in the art will recognize, or be able to ascertain, using no more than routine experimentation, numerous equivalents to the specific embodiments described herein. Such equivalents are intended to be encompassed in the scope of the following claims.

What is claimed is:

1. A method of further reducing nocturnal voids in a male patient in need thereof comprising:
   measuring the patient's serum sodium level;
   administering to the patient, with a serum sodium level of at least 130 mmol/L, prior to bedtime an orodispersible dose of desmopressin chosen from 25 µg, 50 µg, and 100 µg over a first treatment period of about 28 days, wherein the dose is taken from 0.8 to 3 hours prior to the patient's bedtime and once daily;
   measuring the patient's serum sodium level after the first treatment period; and
   continuing to administer the orodisperible dose of desmopressin prior to bedtime over a second contiguous treatment period of at least 28 days to about 1 year if the male patient has a serum sodium level of at least 130 mmol/L,
   wherein the nocturnal voids over the second treatment period are further reduced in view of the reduction in the nocturnal voids over the first treatment period and wherein the reduction in the nocturnal voids over the first treatment period is determined based on the patient's nocturnal voids before administration of the orodispersible dose of desmopressin for the first treatment period.

2. The method according to claim 1, wherein the dose of desmopressin free base is supplied in the form of the acetate salt of desmopressin.

3. The method according to claim 1, wherein the orodispersible dose of desmopressin is a dosage form comprising desmopressin acetate, gelatin, mannitol, and citric acid.

4. The method according to claim 1, wherein the patient in need thereof has nocturia or nocturnal polyuria.

5. The method according to claim 1, wherein the reduction in nocturnal voids ranges from about one nocturnal void to about two nocturnal voids compared to the patient's nocturnal voids before administration of the dose.

6. The method according to claim 1, wherein the second contiguous treatment period ranges from about 8 weeks to about 1 year.

7. The method according to claim 1, wherein the second contiguous period is selected from about 8 weeks, about 12 weeks, about 20 weeks, about 28 weeks, and about 52 weeks.

8. The method according to claim 7, wherein the second contiguous period is about 8 weeks.

9. The method according to claim 7, wherein the second contiguous period is about 20 weeks.

10. The method according to claim 7, wherein the second contiguous period is about 52 weeks.

11. The method according to claim 1, wherein the second contiguous treatment period is about 1 year.

12. The method according to claim 1, wherein the dose is taken without water.

13. The method according to claim 1, wherein the dose is taken approximately 1 hour prior to the patient's bedtime.

* * * * *